United States Patent
Aoki et al.

(10) Patent No.: US 12,156,954 B2
(45) Date of Patent: Dec. 3, 2024

(54) COMPOSITION FOR HARD TISSUE REPAIR AND KIT FOR HARD TISSUE REPAIR

(71) Applicant: MITSUI CHEMICALS, INC., Tokyo (JP)

(72) Inventors: Shinya Aoki, Yokohama (JP); Jingjing Yang, Chiba (JP); Aya Nakagawa, Chiba (JP); Kengo Goto, Ichihara (JP); Takashi Miura, Chiba (JP); Ayako Bando, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 854 days.

(21) Appl. No.: 16/982,192

(22) PCT Filed: Mar. 5, 2019

(86) PCT No.: PCT/JP2019/008554
§ 371 (c)(1),
(2) Date: Sep. 18, 2020

(87) PCT Pub. No.: WO2019/181477
PCT Pub. Date: Sep. 26, 2019

(65) Prior Publication Data
US 2021/0023260 A1    Jan. 28, 2021

(30) Foreign Application Priority Data

Mar. 20, 2018 (JP) ................................ 2018-053013
Jun. 13, 2018 (JP) ................................ 2018-112503
Oct. 25, 2018 (JP) ................................ 2018-200808

(51) Int. Cl.
*A61L 24/06* (2006.01)
*A61K 31/7036* (2006.01)
*A61K 49/04* (2006.01)
*A61L 24/00* (2006.01)

(52) U.S. Cl.
CPC .......... *A61L 24/06* (2013.01); *A61K 31/7036* (2013.01); *A61K 49/0404* (2013.01); *A61L 24/001* (2013.01); *A61L 24/0015* (2013.01); *A61L 2300/102* (2013.01); *A61L 2300/232* (2013.01); *A61L 2300/404* (2013.01); *A61L 2430/02* (2013.01)

(58) Field of Classification Search
CPC ............. A61L 2430/00; A61L 2430/04; A61L 2430/06; A61L 24/06
See application file for complete search history.

(56) References Cited

U.S. PATENT DOCUMENTS

| | | |
|---|---|---|
| 2003/0032964 A1 | 2/2003 | Watkins et al. |
| 2004/0157954 A1 | 8/2004 | Imai et al. |
| 2012/0129970 A1 | 5/2012 | Li et al. |
| 2012/0219544 A1* | 8/2012 | Asada ................ A61L 15/58 514/10.9 |
| 2012/0225012 A1 | 9/2012 | Asada et al. |
| 2015/0099817 A1 | 4/2015 | Ruppert et al. |
| 2016/0058906 A1 | 3/2016 | Truckai et al. |
| 2017/0173210 A1 | 6/2017 | Vogt et al. |
| 2020/0030484 A1 | 1/2020 | Goto et al. |
| 2020/0030485 A1 | 1/2020 | Aoki et al. |

FOREIGN PATENT DOCUMENTS

| | | |
|---|---|---|
| EP | 2 402 041 A1 | 1/2012 |
| EP | 2 821 086 A1 | 1/2015 |
| EP | 3 184 126 A1 | 6/2017 |
| JP | H08224294 A | 9/1996 |
| JP | 2007054619 A | 3/2007 |
| JP | 2008013588 A | 1/2008 |
| JP | 2013535532 A | 9/2013 |
| JP | 2014237821 A | 12/2014 |
| JP | 2019-213697 A | 12/2019 |
| WO | 2011062227 A1 | 5/2011 |
| WO | 2013/129292 A1 | 9/2013 |
| WO | 2015/046100 A1 | 4/2015 |
| WO | 2018/181821 A1 | 10/2018 |
| WO | 2018/181822 A1 | 10/2018 |

OTHER PUBLICATIONS

Miyaguchi et al. "Human monocyte response to retrieved polymethylmethacrylate particles" vol. 62, Issue3, Dec. 5, 2002, pp. 331-337 (Year: 2002).*

International Search Report with an English translation thereof, and Written Opinion issued on May 28, 2019, by the Japanese Patent Office in corresponding International Patent Application No. PCT/JP2019/008554. (9 pages).

* cited by examiner

*Primary Examiner* — James W Rogers
(74) *Attorney, Agent, or Firm* — BUCHANAN, INGERSOLL & ROONEY PC

(57) ABSTRACT

The application discloses a composition for hard tissue repair comprising a monomer (A), a polymer powder (B) and a polymerization initiator (C), wherein the polymer powder (B) comprises a polymer powder (B-x) having an aspect ratio of 1.10 or more, and the cumulative ratio of powder particles having aspect ratios of 1.00 or more and less than 1.10 in all of the powder particles contained in the composition for hard tissue repair is 75 cumulative % or less, as well as, a kit for hard tissue repair comprising three or more members, in which each of the components of the monomer (A), the polymer powder (B) and the polymerization initiator (C) contained in this composition for hard tissue repair are divided and contained in the members in an optional combination.

7 Claims, No Drawings

COMPOSITION FOR HARD TISSUE REPAIR AND KIT FOR HARD TISSUE REPAIR

TECHNICAL FIELD

The present invention relates to a composition for hard tissue repair and a kit for hard tissue repair excellent in various properties required for a composition for hard tissue repair, which properties include, for example, adhesion to an adherend such as an artificial joint etc., penetrability into an adherend such as cancellous bone etc., and reduction of amount of eluted monomers.

BACKGROUND ART

Various compositions for hard tissue repair have been investigated as a bone cement for fixing hard tissue such as bones and cartilages, etc., to an artificial joint; a bone filler used for osteoporosis treatment etc.; and an artificial bone material. For example, such compositions thus investigated include a composition containing polymethyl methacrylate, methyl methacrylate, and benzoyl peroxide (polymerization initiator); as well as a composition containing a (meth) acrylate, an inorganic filler, such as calcium phosphate, etc., and an organic peroxide (for example, Patent Document 1). However, such compositions cause large heat generation upon curing, and have a high risk of damaging the affected tissue.

As a composition for hard tissue repair which has improved the above point, for example, Patent Document 2 discloses a composition for hard tissue repair containing a (meth)acrylate (A), a (meth)acrylate polymer (B) and a specific polymerization initiator (C). This composition generates a little heat upon curing and is also excellent in workability.

RELATED ART DOCUMENTS

Patent Documents

Patent Document 1: Japanese Unexamined Patent Application Publication (JP-A) No. 8-224294; JP. 08-224294 (1996)
Patent Document 2: International Publication WO 2011/062227

SUMMARY OF INVENTION

Technical Problem

When a composition for hard tissue repair is used to fix, for example, an artificial joint and a bone, the composition for hard tissue repair in a soft mass (dough) form before hardening is implanted in the medullary cavity, and pressed and deformed, and then, completely hardened (polymerized).

A composition for hard tissue repair is usually prepared by mixing a plurality of components immediately before use at a site of use (for example, a site to be treated). Just after mixing of the components, the composition for hard tissue repair forms a slurry, which becomes sticky and sticks with stringiness to latex gloves of the user (e.g., practitioner). Then, after a period of time from the preparation, the composition for hard tissue repair becomes a soft mass (dough) form. Specifically, the point of time when this soft mass (dough) is formed is qualitatively identified as the point of time when the composition in the soft mass form has no more stringiness and does not stick to the latex glove of the user. Since the composition for hard tissue repair in a soft mass (dough) form has appropriate viscosity and fluidity, such composition is easy to handle, and exhibits good fixing force even after implantation.

A composition for hard tissue repair is generally used at the stage of the soft mass (dough) form as described above. The phenomenon that the composition for hard tissue repair becomes a soft mass (dough) form is usually referred to as "Kijika" as a Japanese word meaning "dough formation" or "doughing", and the time to reach a soft mass (dough) form is usually called "dough time".

A composition for hard tissue repair having a long dough time is inferior in operating efficiency. Further, it is difficult to handle a composition for hard tissue repair before completion of the dough formation. Moreover, when a composition for hard tissue repair before completion of dough formation is implanted in, for example, medullary cavity, the composition cannot maintain a shape suitable for fixing the artificial joint and the bone, and a gap is formed at the interface between the composition and the artificial joint and/or the bone tissue. As a result, it is likely to cause insufficient fixation of the artificial joint. This insufficient fixation is considered to easily induce loosening or wear of the artificial joint, which further cause pain or infection of the patient. Moreover, when revision surgery of the artificial joint is required, the patient takes a large physical burden. Therefore, poor adhesion between the composition for hard tissue repair formed as a dough and the artificial joint, as well as poor penetrability of the dough into the bone tissue are undesirable from the viewpoint of safety ensuring for the patient and reduction of the burden.

Further, the present inventors considered that there was room for improvement on the conventional compositions for hard tissue repair in terms of macroscopic adhesion to bone tissue. For example, if a bone cement (as a composition for hard tissue repair) has poor penetrability into the cancellous bone, a gap occurs on the interface to the bone, which causes pain due to osteolysis. If such symptom gets worse, a revision surgery is necessary.

Further, there is a possibility every time that an unpolymerized monomer component contained in the composition for hard tissue repair also remains in the polymer, which is eluted in the living body. For example, it is known that, when the monomers remaining in a composition for hard tissue repair are eluted into a living body, the monomers are harmful against the tissues and cells of the living body, which furthermore cause a drop in blood pressure. In particular, when the drop in blood pressure due to the monomer elution in the living body occurs in addition to a drop in blood pressure caused by the other reasons during the treatment, it is likely to cause arrhythmia and myocardial ischemia. Such a large amount of the eluted monomers is not desirable from the viewpoint of safety ensuring for the patient during its use (during treatment) and after its use (after treatment).

The object of the present invention is to provide a composition for hard tissue repair and a kit for hard tissue repair excellent in various properties required for a composition for hard tissue repair, which properties include, for example, adhesion to an adherend such as an artificial joint etc., penetrability into an adherend such as cancellous bone etc., and reduction of amount of eluted monomers.

Solution to Problem

The present inventors have intensively investigated to achieve the above-described object and resultantly found that it was very effective to use a polymer powder (B) comprising a polymer powder having an aspect ratio within a specific range, and to optimize the cumulative ratio concerning the aspect ratios regarding all of the particles contained in the composition for hard tissue repair. Thus, the present inventors have completed the present invention based on the above findings, i.e., the present invention is defined by the following matters:

[1] A composition for hard tissue repair comprising a monomer (A), a polymer powder (B) and a polymerization initiator (C), wherein
the polymer powder (B) comprises a polymer powder (B-x) having an aspect ratio of 1.10 or more, and
the cumulative ratio of powder particles having aspect ratios of 1.00 or more and less than 1.10 in all of the powder particles contained in the composition for hard tissue repair is 75 cumulative % or less.

[2] The composition for hard tissue repair according to [1], wherein the cumulative ratio of powder particles having aspect ratios of 1.00 or more and less than 1.10 in all of the powder particles contained in the composition for hard tissue repair is 2.5 cumulative % or more, and 65 cumulative % or less.

[3] The composition for hard tissue repair according to [1], wherein the polymer powder (B) comprises a polymer powder (B-x) having an aspect ratio of 1.10 or more and 1.90 or less, and the aspect ratio of all of the polymer powder (B) is 1.11 or more and 1.80 or less.

[4] The composition for hard tissue repair according to [1], wherein the monomer (A) is a (meth)acrylate-based monomer.

[5] The composition for hard tissue repair according to [1], wherein the polymer powder (B) is a (meth)acrylate-based polymer powder.

[6] The composition for hard tissue repair according to [1], wherein the polymerization initiator (C) comprises an organic boron compound (c1).

[7] The composition for hard tissue repair according to [1], comprising 10 to 45 parts by mass of the monomer (A), 54.9 to 80 parts by mass of the polymer powder (B), and 0.1 to 10 parts by mass of the polymerization initiator (C) (the sum of the components (A) to (C) is taken as 100 parts by mass).

[8] The composition for hard tissue repair according to [1], further comprising a contrast medium (X).

[9] The composition for hard tissue repair according to [8], wherein the blending amount of the contrast medium (X) is 0.01 to 70 parts by mass (the sum of the components (A) to (C) is taken as 100 parts by mass).

[10] The composition for hard tissue repair according to [1], further comprising antimicrobial drug particles (Y).

[11] The composition for hard tissue repair according to [10], wherein the blending amount of the antimicrobial drug particles (Y) is 0.01 to 30 parts by mass (the sum of the components (A) to (C) is taken as 100 parts by mass).

[12] A kit for hard tissue repair comprising three or more members, in which each of the components of the monomer (A), the polymer powder (B) and the polymerization initiator (C) contained in the composition for hard tissue repair according to [1] are divided and contained in the members in an optional combination.

Advantageous Effect of invention

According to the present invention, a composition for hard tissue repair and a kit for hard tissue repair can be provided, which are excellent in various properties required for a composition for hard tissue repair, which properties include, for example, adhesion to an adherend such as an artificial joint etc., penetrability into an adherend such as cancellous bone etc., and reduction of amount of eluted monomers.

DESCRIPTION OF EMBODIMENTS

[Monomer (A)]

The monomer (A) used in the present invention is not particularly limited as long as the monomer can be polymerized by the polymerization initiator (C) described later. As the monomer (A), any one of monofunctional monomers and polyfunctional monomers can be used depending on the purpose of use.

As the monomer (A), for example, (meth)acrylate-based monomers and other vinyl compounds can be used. Among them, (meth)acrylate-based monomers are preferable in terms of relatively low stimulation to the human body. In the present invention, "(meth)acrylate" is a generic term for acrylate and methacrylate. In general, an acidic group-containing monomer is excellent in adhesion to a hard tissue. Since the monomer having an acidic group acts also as a decomplexing agent described later, polymerization reaction can be initiated by using the acidic group-containing monomer, when an alkylborane-amine complex is used as a polymerization initiator (C). Thus, for example, the adhesion can also be improved by using an appropriate amount of an acidic group-containing monomer in combination with a (meth)acrylate-based monomer having no acidic group.

Concrete examples of the monofunctional (meth)acrylate-based monomer having no acidic group include (meth)acrylic acid alkyl esters such as methyl (meth)acrylate, ethyl (meth)acrylate, propyl (meth)acrylate, butyl (meth)acrylate, hexyl (meth)acrylate, 2-ethylhexyl (meth)acrylate, dodecyl (meth)acrylate, lauryl (meth)acrylate, cyclohexyl (meth)acrylate, benzyl (meth)acrylate and isobornyl (meth)acrylate; hydroxyalkyl esters of (meth)acrylic acid such as 2-hydroxyethyl (meth)acrylate, 2-hydroxypropyl (meth)acrylate, 3-hydroxypropyl (meth)acrylate, 4-hydroxybutyl (meth)acrylate, 5-hydroxypentyl (meth)acrylate, 6-hydroxyhexyl (meth) acrylate, 1,2-dihydroxypropyl mono(meth)acrylate, 1,3-dihydroxypropyl mono(meth)acrylate and erythritol mono(meth)acrylate; polyalkylene glycol mono (meth)acrylates such as diethylene glycol mono(meth)acrylate, triethylene glycol mono(meth)acrylate, polyethylene glycol mono(meth)acrylate and polypropylene glycol mono (meth)acrylate; (poly)alkylene glycol monoalkyl ether (meth)acrylates such as ethylene glycol monomethyl ether (meth)acrylate, ethylene glycol monoethyl ether (meth)acrylate, diethylene glycol monomethyl ether (meth)acrylate, triethylene glycol monomethyl ether (meth)acrylate, polyethylene glycol monomethyl ether (meth)acrylate and polypropylene glycol monoalkyl ether (meth)acrylate; fluoroalkyl esters of (meth)acrylic acid such as perfluorooctyl (meth)acrylate and hexafluorobutyl (meth)acrylate; silane compounds having a (meth)acryloxyalkyl group such as γ-(meth)acryloxypropyltrimethoxysilane and γ-(meth)acryloxypropyltri(trimethylsiloxy) silane; and, (meth)acrylates having a hetero ring such as tetrahydrofurfuryl (meth)acrylate.

Concrete examples of the polyfunctional (meth)acrylate-based monomer having no acidic group include poly(meth)acrylates of alkane polyols such as ethylene glycol di(meth)acrylate, propylene glycol di(meth)acrylate, butylene glycol di(meth)acrylate, neopentyl glycol di(meth)acrylate, hexylene glycol di(meth)acrylate, trimethylolpropane tri(meth)acrylate and pentaerythritol tetra(meth)acrylate; polyoxyalkane polyol poly(meth)acrylates such as diethylene glycol di(meth)acrylate, triethylene glycol di(meth)acrylate, polyethylene glycol di(meth)acrylate, dipropylene glycol di(meth)acrylate, polypropylene glycol di(meth)acrylate, dibutylene glycol di(meth)acrylate and dipentaerythritol hexa (meth)acrylate; alicyclic or aromatic di(meth)acrylates represented by the following general formula (1):

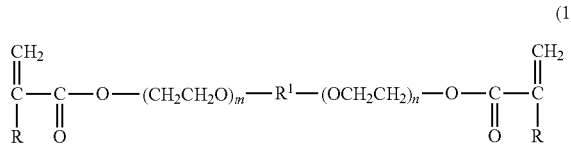

(in the formula (1), R is a hydrogen atom or a methyl group, m and n are each independently a number of 0 to 10, and $R^1$ is any one of

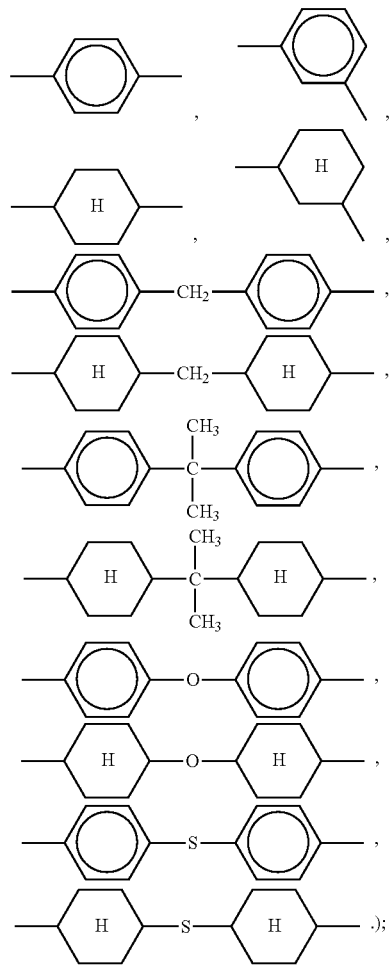

);

alicyclic or aromatic epoxy di(meth)acrylates represented by the following general formula (2):

(in the formula (2), R, n and $R^1$ have the same meaning as R, n and $R^1$ in the above-described formula (1)); and polyfunctional (meth)acrylates having a urethane bond in the molecule represented by the following formula (3):

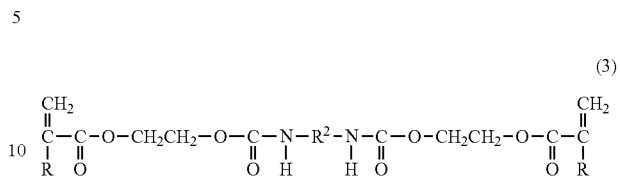

(in the formula (3), R has the same meaning as R in the above-described formula (1), and $R^2$ is any one of

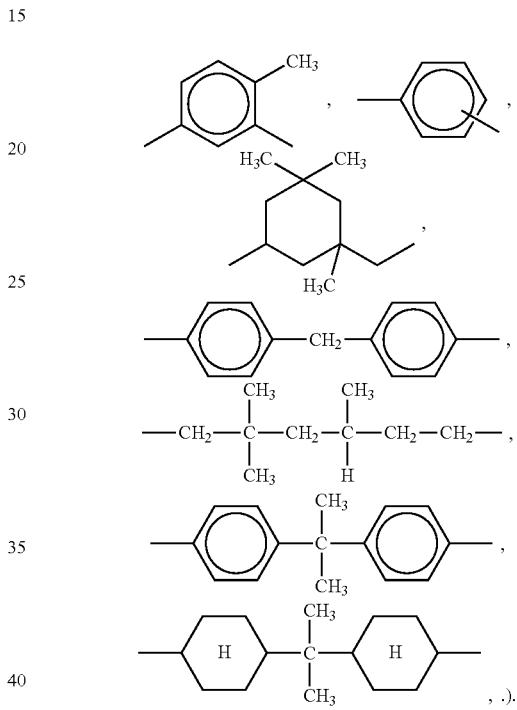

, .).

In the above concrete example compounds, preferable monofunctional (meth)acrylate-based monomers include alkyl (meth)acrylates such as methyl (meth)acrylate and ethyl (meth)acrylate; hydroxyalkyl esters of (meth)acrylic acid such as 2-hydroxyethyl (meth)acrylate, 1,3-dihydroxypropyl mono(meth)acrylate and erythritol mono(meth)acrylate; and polyethylene glycol mono (meth)acrylates such as triethylene glycol monomethyl ether (meth)acrylate and triethylene glycol mono(meth)acrylate.

In the above concrete example compounds, preferable polyfunctional (meth)acrylate-based monomers include di(meth)acrylates having an ethylene glycol chain in the molecule such as triethylene glycol di(meth)acrylate and polyethylene glycol di(meth)acrylate; compounds represented by the following formula (1)-a:

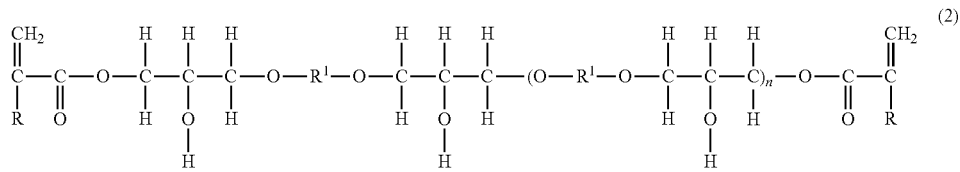

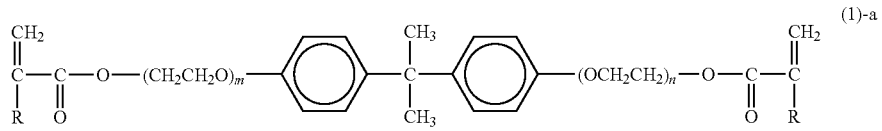

(in the formula (1)-a, R, m and n have the same meaning as R, m and n in the above-described formula (1));
compounds represented by the following formula (2)-a:

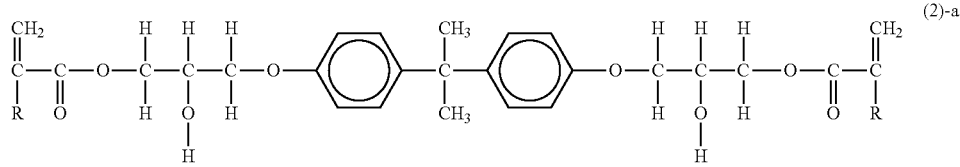

(in formula (2)-a, R has the same meaning as R in the above-described formula (1)); and
compounds represented by the following formula (3)-a:

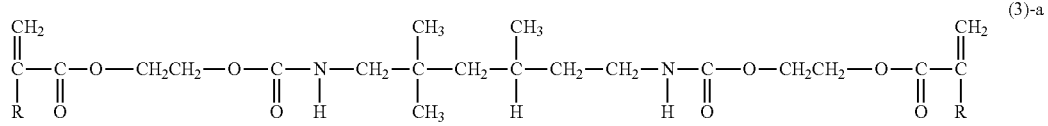

(in the formula (3)-a, R is the same as R in the above-described formula (1)).

Two or more of these (meth)acrylate-based monomers may be used in combination.

Concrete examples of the monomer having an acidic group(s), i.e., the acidic group-containing monomer, include monomers having a carboxylic acid group(s) or an anhydride group(s) thereof such as (meth)acrylic acid and an anhydride thereof, 1,4-di(meth)acryloxyethylpyromellitic acid, 6-(meth)acryloxyethylnaphthalene-1,2,6-tricarboxylic acid, N-(meth)acryloyl-p-aminobenzoic acid, N-(meth)acryloyl-o-aminobenzoic acid, N-(meth)acryloyl-m-aminobenzoic acid, N-(meth)acryloyl-5-aminosalicylic acid, N-(meth)acryloyl-4-aminosalicylic acid, 4-(meth) acryloxyethyltrimellitic acid and an anhydride thereof, 4-(meth) acryloxybutyltrimellitic acid and an anhydride thereof, 4-(meth)acryloxyhexyltrimellitic acid and an anhydride thereof, 4-(meth)acryloxydecyltrimellitic acid and an anhydride thereof, 2-(meth) acryloyloxybenzoic acid, 3-(meth) acryloyloxybenzoic acid, 4-(meth)acryloyloxybenzoic acid, β-(meth)acryloyloxyethyl hydrogen succinate, β-(meth) acryloyloxyethyl hydrogen maleate, β-(meth)acryloyloxyethyl hydrogen phthalate, 11-(meth)acryloyloxy-1,1-undecanedicarboxylic acid and p-vinylbenzoic acid; monomers having a phosphate group such as (2-(meth)acryloxyethyl) phosphoric acid, (2-(meth) acryloxyethylphenyl) phosphoric acid and 10-(meth)acryloxydecylphosphoric acid; and monomers having a sulfonate group such as p-styrenesulfonic acid and 2-acrylamide-2-methylpropanesulfonic acid. In the above monomers, 4-methacryloxyethyl trimellitic acid and an anhydride thereof are preferable.

Two or more of the acidic group-containing monomers may be used in combination. The acidic group-containing monomers can also be used as a calcium salt form.

The blending amount of the monomer (A) is preferably 10 to 45 parts by mass, more preferably 20 to 45 parts by mass, more preferably 25 to 36 parts by mass (the sum of the components (A) to (C) is taken as 100 parts by mass). The lower limit value of each of the above ranges is significant in terms of expression of the properties such as coating easiness, handling, penetrability into bone tissue, etc. The upper limit value is significant in terms of expression of properties such as adhesive strength, mechanical properties, toughness, etc., and/or, in terms of capability of reducing the amount of the residual monomers and/or the amount of eluted monomers. When the monomer (A) comprises an acidic group-containing monomer(s), the amount of the acidic group-containing monomer(s) is preferably 0.005 to 30% by mass, more preferably 0.01% to 25% by mass with respect to 100% by mass of the sum of the monomer (A). However, the use of the acidic group-containing monomer (s) is optional, and the composition for hard tissue repair of the present invention may or may not contain the acidic group-containing monomer(s).

[Polymer Powder (B)]

Although the type of the polymer powder (B) used in the present invention is not particularly limited, it is preferable that a part or all of the monomer units forming the polymer powder (B) originates from the same kind of monomers as a part or all of the monomer (A) as described above. In the present invention, "the polymer" is a general term for homopolymers and copolymers. As the polymer powder (B), for example, (meth)acrylate-based polymers and other vinyl polymers can be used. Among them, (meth)acrylate-based polymers are preferable.

Concrete examples of the (meth)acrylate-based polymer include non-crosslinked polymers such as polymethyl (meth)acrylate, polyethyl (meth)acrylate, methyl (meth)acrylate-ethyl (meth)acrylate copolymer, methyl (meth)acrylate-butyl (meth)acrylate copolymer and methyl (meth)acrylate-styrene copolymer; cross-linked polymers such as methyl (meth)acrylate-ethylene glycol di(meth)acrylate copolymer, methyl (meth)acrylate-triethylene glycol di(meth)acrylate copolymer and methyl (meth)acrylate-butadiene-based monomer copolymer, and these polymers partially forming a calcium salt. The polymer powder may be an organic/inorganic composite in which a metal oxide or a metal salt is coated with a non-crosslinked polymer or a crosslinked polymer.

As the polymer powder (B), one kind of polymer powder may be used alone, or a mixture of plural kinds of polymer powder may be used.

In the present invention, the polymer powder (B) comprises a polymer powder (B-x) having an aspect ratio of 1.10 or more, and the cumulative ratio of powder particles having aspect ratios of 1.00 or more and less than 1.10 in all of the powder particles contained in the composition for hard tissue repair is 75 cumulative % or less. The effects relating to the various properties (e.g., adhesion to an adherend such as an artificial joint, etc., penetrability into an adherend such as cancellous bone, etc., and reduction of the amount of eluted monomers) by the present invention are mainly obtained by the above particle characteristics.

In the present invention, "adhesion" means the adhesive strength and/or the close contact strength of the composition for hard tissue repair to an adherend such as an artificial joint, a bone tissue, etc. For example, even when the adherend such as an artificial joint, etc., is made of a metal, the composition for hard tissue repair of the present invention exhibits excellent close contact, while the type of adherend is not limited to this. The composition for hard tissue repair of the present invention expresses excellent close contact also in its use, for examples, as a bone cement for adhesion between hard tissues parts, filling it into hard tissues, adhesion and/or close contact between hard tissue and a metallic artifact, adhesion and/or close contact between hard tissue and the other tissues such as soft tissue, etc., and fixing hard tissue, such as bones, cartilages, etc., to an artificial joint; a filler for bone defect; a bone replacement material; an artificial bone, etc. The reason why the effects of the present invention can be obtained will be described below.

(Adhesion to Adherend Such as Artificial Joint, etc.)

Generally, the molecular structure of the polymer powder (B) is similar to that of the monomer (A), so that the polymer powder (B) is partially dissolved in the monomer (A). Therefore, the mixed solution is rapidly thickened, as compared with the case of thickening accompanying the polymerization reaction alone. Further, it is generally known that when the viscosity of the mixed solution becomes high, it becomes difficult to occur the termination reaction between the growing radical species and, thus, the polymerization rate becomes fast. This is called as the cage effect ("Trommsdorff effect").

Since the polymer powder (B-x) having a large aspect ratio (an aspect ratio(s) of 1.10 or more) used in the present invention is more easily soluble in the monomer (A) than the polymer powder (B-y) having a small aspect ratio (an aspect ratio of 1.00 or more and less than 1.10), the composition is rapidly thickened and the dough time tends to be shortened due to the effect of accelerating the polymerization rate by the cage effect.

Further, in the present invention, the cumulative ratio (%) of powder particles having aspect ratios of 1.00 or more and less than 1.10 in all of the powder particles is appropriately low. Thus, the proportion of powder particles having a large aspect ratio(s) (powder particles having an aspect ratio of 1.10 or more) is moderately high. Among powder particles having such a large aspect ratio, the polymer powder (B-x) having particularly such a large aspect ratio exhibits the effect of shortening the dough time as previously described. Further, although the powder particles having such a large aspect ratio were made of an material insoluble in the monomer (A), the powder particles having such a large aspect ratio due to their shapes tend to increase the viscosity of the composition, as compared with powder particles having such a small aspect ratio. Accordingly, when the proportion of the powder particles having such a large aspect ratio is higher, the dough time tends to be further shortened.

The shorter dough time means that the time is shorter until each of the components are uniformly mixed in the desired blending ratio to form a homogeneous soft mass. There is tendency that a composition for the hard tissue repair excellent in homogeneity is also excellent in operability, and substantial reduction of the contact area with an adherend such as an artificial joint, etc., is suppressed, in comparison with a composition inferior in homogeneity. Moreover, the composition for hard tissue repair having excellent homogeneity has a desired composition (optimal blending ratio from the viewpoint of each of the properties) at any positions. It is considered, from these points, that the anchoring effect associated with the polymerization reaction of the composition is sufficiently exhibited, and the effect of improving the adhesion to the adherend such as an artificial joint, etc., in a soft mass (dough) form, is obtained.

(Penetrability into Adherend Such as Cancellous Bone, etc.)

The composition for hard tissue repair is a slurry-like composition (slurry containing powder and liquid) in which the polymerization reaction has not yet proceeded sufficiently at the stage immediately after preparation. The flow property of this slurry-like composition has a great influence on the penetrability into an adherend such as cancellous bone, etc. Generally, it is known that the slurry-like fluids include Newtonian fluids which are not influenced by shear stress and of which flow property (viscosity) are not changed; and non-Newtonian fluids which are influenced by shear stress and of which flow property are changed. In addition, the non-Newtonian fluids include fluids exhibiting dilatancy. The dilatancy is a characteristic that the fluid viscosity increases when the shear stress increases. For example, when a slurry-like composition is allowed to penetrate into an adherend such as cancellous bone, etc., shear stress is generated at the contact surface between the fluid and the adherend. Therefore, a fluid exhibiting a remarkable dilatancy is not preferable as the composition for hard tissue repair, because the viscosity increases during its penetration into the adherend.

It is considered that the polymer powder (B-x) having such a large aspect ratio used in the present invention tends to be difficult to generate less gaps between the particles even when external stress is applied, as compared with a polymer powder having such a small aspect ratio. Such fluid, which is not likely to form gaps, is considered to be difficult to express dilatancy. Further, it is considered that any powder particles having such a large aspect ratio other than the polymer powder (B-x) also tend to be unlikely to generate gaps between particles, and the fluid is also not likely to express dilatancy. As a result, an increase in the viscosity of the slurry-like composition is suppressed, and the penetrability into an adherend such as cancellous bone is improved.

(Reduction of Amount of Eluted Monomer)

As described above, in general, the mixed liquid of the polymer powder (B) and the monomer (A) is rapidly thickened as compared with the case of thickening accompanying the polymerization reaction alone. Additionally, the cage effect also makes the polymerization rate higher. As a result, the eluted amount of unpolymerized monomers from the surface of the composition for hard tissue repair is usually reduced.

However, when water is present in an excess amount in the living body, the polymerization activity of the polymerization initiator (C) is easily lowered. Thus, the polymerization per se is easily inhibited. There is also tendency that, since the solubility of the polymer powder (B) in the monomer (A) is lowered due to the influence of water which has large difference from the polymer powder (B) in their molecule structure, the cage effect is not sufficiently exhibited. In this case, the amount of the eluted monomers cannot be reduced sufficiently.

On the other hand, in the present invention, since the polymer powder (B-x) having such a large aspect ratio is easily dissolved in the monomer (A), a decrease in the solubility of the polymer powder (B) in the monomer (A) tends to be suppressed even in the presence of water in an excess amount in the living body. As a result, it is considered that the cage effect is sufficiently exhibited, the polymerization reaction is promoted, and the amount of eluted monomers is reduced.

Furthermore, when an organic boron compound (C1) described later, for example, is used as the polymerization initiator (C), the polymerization reaction proceeds from the interface with the body fluid or the spinal fluid contained in a living tissue, to which the implanted composition for hard tissue repair is directly contacted. As a result, it is considered that the amount of unpolymerized monomers further decreases and, thus, the amount of eluted monomers is reduced. The reason why the polymerization reaction proceeds from the interface is assumed that the polymerization activity is increased or maintained by the dissolved oxygen contained in the water existing at the interface with the body fluid or the spinal fluid.

(Other Property 1: Shortening of Dough Time)

As described above, in general, the mixed liquid of the polymer powder (B) and the monomer (A) rapidly thickens as compared with the case of thickening accompanying the polymerization reaction alone. Additionally, the cage effect also makes the polymerization rate higher. As a result, the dough time tends to be shortened, as described above.

(Other Property 2: Reduction of Residual Monomer Amount)

As described above, since the polymer powder (B-x) having such a large aspect ratio is easily dissolved in the monomer (A), even if water is present in an excess amount in the living body, a decrease in the solubility of polymer powder (B) in the monomer (A) tends to be suppressed. As a result, it is considered that the cage effect is sufficiently expressed, the polymerization reaction is promoted, and the residual monomer amount is reduced.

(Other Property 3: Discharging Performance from Equipment for Filling)

For example, when a slurry-like fluid is discharged from a discharge nozzle, shear stress generates on the contact surface between the fluid and the adherend. As a result, pressure loss (energy loss) occurs. In particular, regarding the general equipment for filling such as an orthopedic cement mixer, an orthopedic cement injector, an orthopedic cement dispenser, a cement gun, etc., the inner diameter (cross-sectional area) is remarkably reduced from the syringe portion (large diameter portion) to the discharge nozzle portion (small diameter portion). In such a case, when the composition for hard tissue repair exhibits dilatancy remarkably, the discharging performance lowers by increase of the pressure loss (energy loss) at the site with reduction of the cross-sectional area. On the other hand, there is a tendency that the polymer powder (B-x) having such a large aspect ratio and the other powder particles having such a large aspect ratio, used in the present invention, are unlikely to form gaps between the particles. Thus, it is considered that dilatancy is difficult to be expressed, as described above. As a result, the increase in the viscosity of the slurry-like composition is suppressed and the discharging performance tends to be improved.

(Other Property 4: Toughness)

In general, destruction of a hardened composition for hard tissue repair after curing occurs due to stress concentration generated at the defects contained in the composition. The examples of the defects include those due to impurities contained in each component of the monomer (A), the polymer powder (B), the polymerization initiator (C), etc.; those due to additive components such as the contrast medium (X), a colorant, etc.; those due to ununiform structures such as gaps, voids, weld lines, etc., which occur during the mixing work to prepare a composition for hard tissue repair; and those due to ununiform higher-order structures of high molecular weight components contained in the composition after curing. The physical property values usable as an index of resistance against the initiation and progress of the destruction of the composition include "fracture toughness value". Further, in general, the methods of improving the fracture toughness of a resin material include those of adding various components such as rubber particles, a thermoplastic resin, an inorganic filler, etc. It is important that the interface between the additive components and the resin material is firmly adhered and/or closely contacted. When the physical properties between the additive components and the resin material are significantly different, the adhesion and/or the close contact on their interface tend to be insufficient. Thus, there is a tendency that interfacial peeling easily occurs and, thus, its fracture toughness value declines. On the other hand, according to the present invention, it is easy to select the type of the polymer powder (B) based on the type of the monomer (A), i. e., the polymer powder (B) can be easily selected, which is the same as or similar to the monomer (A) in their fundamental molecular structures. When their fundamental molecular structures are the same or similar, the uniformity of the interface formed by the composition for hard tissue repair thus prepared is excellent, and, thus, the interfacial peeling is difficult to occur. Furthermore, when the polymer powder (B-x) having such a large aspect ratio is used, although cracks occur in the composition, the effects due to physical wedging and/or bridging become easily apparent, in comparison with a composition containing a polymer powder having such a small aspect ratio used alone and, thus, progress of the cracks tends to be suppressed. It is considered that such improvement of the effects relating to the toughness is expressed by suppression of the crack progress.

The polymer powder (B) may comprise, for example, only a polymer powder (B-x), i. e., consists of a polymer (B-x), having an aspect ratio of 1.10 or more, and preferably comprises, particularly, a polymer powder (B-x) having an aspect ratio of 1.10 or more and a polymer powder (B-y) having an aspect ratio of 1.00 or more and less than 1.10 from a viewpoint of improvement of various properties (for example, the properties explained above) as required for the composition for hard tissue repair. The blending amount of the polymer powder (B-x) and the polymer powder (B-y) will be described below.

Regarding various properties such as adhesion to an adherend (e.g., artificial joint), etc., when the polymer powder (B-x) and the polymer powder (B-y) are mixed to prepare 100% by mass of the polymer powder (B), the blending amount of the polymer powder (B-x) is preferably 3.0% by mass or more, more preferably 4.0 to 70% by mass, and more preferably 5.0 to 60% by mass. The blending amount of the polymer powder (B-y) is preferably 97.0% by mass or less, more preferably 30 to 96.0% by mass, and more preferably 40 to 95.0% by mass. It is preferable to use the polymer powder (B-x) having such a large aspect ratio in such a specific amount or more as describe above from a viewpoint of appropriately keeping the solubility of the polymer powder (B) in the monomer (A); expression of a sufficient thickening effect and the cage effect ("Trommsdorff effect"); shortening of the dough time; and improvement of various properties such as the operability of the composition for hard tissue repair, etc. In addition, it is preferable to use the polymer powder (B-x) having such a large aspect ratio in such a specific amount or less as describe above from a view point of suppression of remarkable thickening to enable to prepare a homogeneous composition for hard tissue repair; suppression of reduction of the anchoring effect with substantial reduction of the contact area with an adherend; and improvement of various properties such as adhesion with an adherend (e.g., artificial joint), etc.

Further, regarding various properties such as penetrability into an adherend (e.g., cancellous bone), etc., when the polymer powder (B-x) and the polymer powder (B-y) are mixed to prepare 100% by mass of the polymer powder (B), the blending amount of the polymer powder (B-x) is preferably 1.0 to 45% by mass, more preferably 6.0 to 45% by mass, and more preferably 10 to 45% by mass. The blending amount of the polymer powder (B-y) is preferably 55 to 99.0% by mass, more preferably 55 to 94.0% by mass, and more preferably 55 to 90% by mass. It is preferable to use the polymer powder (B-x) having such a large aspect ratio in such a specific amount or more as described above from a viewpoint of suppression of the expression of dilatancy, improvement of various properties such as penetrability into an adherend (e.g., cancellous bone), etc. In addition, it is preferable to use the polymer powder (B-x) having such a large aspect ratio in such a specific amount or less as describe above from a viewpoint of suppression of remarkable thickening and improvement of various properties such as penetrability into an adherend (e.g., cancellous bone), etc.

Furthermore, regarding various properties such as reduction of the amount of eluted monomers, when the polymer powder (B-x) and the polymer powder (B-y) are mixed to prepare 100% by mass of the polymer powder (B), the blending amount of the polymer powder (B-x) is preferably 1.0 to 70% by mass, more preferably 5.0 to 60% by mass, and more preferably 10 to 55% by mass. The blending amount of the polymer powder (B-y) is preferably 30 to 99.0% by mass, more preferably 40 to 95.0% by mass, and more preferably 45 to 90% by mass. It is preferable to use the polymer powder (B-x) having such a large aspect ratio in such a specific amount or more as described above from a viewpoint of expression of the sufficient cage effect ("Trommsdorff effect") and improvement of various properties such as reduction of the amount of eluted monomers, etc. In addition, it is preferable to use the polymer powder (B-x) having such a large aspect ratio in such a specific amount or less as described above from a viewpoint of suppression of remarkable thickening to enable to prepare a homogenous composition for hard tissue repair; suppression of increase of the ununiform structures on the surface and/or inside of the cured product; and improvement of various properties such as reduction in the amount of eluted monomers, etc.

According to the composition for hard tissue repair of the present invention, it is preferable that the cumulative ratio of the particles having aspect ratios of 1.00 or more and less than 1.10 in the whole polymer particle (B) or all of the powder particles therein is in the specifically defined range, from a viewpoint of improvement of various properties (for example, various properties as explained above) required for the composition for hard tissue repair. Such cumulative ratio will be described below.

Regarding various properties such as adhesion to an adherend (e.g., artificial joint), etc., the cumulative ratio of the polymer powder particles (B-y) having aspect ratio of 1.00 or more and less than 1.10 based on the whole polymer powder (B) (as 100 cumulative %) is preferably 86 cumulative % or less, and more preferably 3.5 to 80 cumulative %. It is preferable to define the cumulative ratio of the polymer powder particles (B-y) having such a small aspect ratio, as such a specific ratio or more as described above from a viewpoint of suppression of remarkable thickening to enable to prepare a homogeneous composition for hard tissue repair; suppression of decrease of the anchoring effect with substantial reduction of the contact area with an adherend; and improvement of various properties such as adhesion with an adherend (e.g., artificial joint), etc. In addition, it is preferable to define the cumulative ratio of the polymer powder particles (B-y) having such a small aspect ratio as such a specific ratio or less as described above from a viewpoint of appropriately keeping the solubility of the polymer powder (B) in the monomer (A); expression of the sufficient thickening effect and cage effect ("Trommsdorff effect"); shortening of the dough time; and improvement of various properties such as operability of the composition for hard tissue repair, etc.

Further, regarding various properties such as penetrability into an adherend (e.g., cancellous bone), etc., the cumulative ratio of the polymer powder particles (B-y) having aspect ratios of 1.00 or more and less than 1.10 based on the whole polymer powder (B) (as 100 cumulative %) is preferably 15 to 55 cumulative %, and more preferably 20 to 50 cumulative %. It is preferable to define the cumulative ratio of the polymer powder particles (B-y) having such a small aspect ratio, as such a specific ratio or more as describe above from a viewpoint of suppression of remarkable thickening and improvement of various properties such as penetrability into an adherend (e.g., cancellous bone), etc. In addition, it is preferable to define the cumulative ratio of the polymer powder particles (B-y) having such a small aspect ratio, as such a specific ratio or less as described above from a viewpoint of suppression of dilatancy expression and improvement of various properties such as penetrability into an adherend (e.g., cancellous bone), etc.

Furthermore, regarding various properties such as reduction of the amount of eluted monomers, etc., the cumulative ratio of the polymer powder particles (B-y) having aspect ratios of 1.00 or more and less than 1.10 in the whole polymer powder (B) (as 100 cumulative %) is preferably 15 to 55 cumulative %, and more preferably 20 to 50 cumulative %. It is preferable to define the cumulative ratio of the polymer powder particles (B-y) having such a small aspect ratio as such a specific ratio or more as described above from a viewpoint of suppression of remarkable thickening to enable to prepare a homogeneous composition for hard tissue repair; suppression of increase of the ununiform structures on the surface and/or inside of the cured product; and improvement of various properties such as reduction of the amount of eluted monomers, etc. In addition, it is preferable to define the cumulative ratio of the polymer powder particles (B-y) having such a small aspect ratio as such a specific ratio or less as described above from a viewpoint of expression of the sufficient cage effect ("Trommsdorff effect") and improvement of various properties such as reduction of the amount of eluted monomers, etc.

The composition for hard tissue repair of the present invention may contain powder particles other than the polymer powder (B) depending on the conditions. In such a case, it is preferable to consider the cumulative ratio (%) of powder particles having aspect ratios of 1.00 or more and less than 1.10 in all of the powder particles in the composition for hard tissue repair. The powder particles other than the polymer powder (B) include, for example, a contrast medium (X), antimicrobial drug particles (Y), and a polymerization initiator (C) as described later. As described below, the polymerization initiator (C) may be either in a liquid form or a solid form (for example, a powder form). The powdery polymerization initiator is mixed with the polymer powder (B) or supported on the polymer powder (B). Therefore, the powdery polymerization initiator corresponds to the powder particles other than the polymer powder (B). Thus, the above term "all of the powder particles" contained in the composition for hard tissue repair may mean that the powder particles consist of all of the polymer powder (B) and the powder particles other than the polymer powder (B) as exemplified above.

Regarding various properties such as adhesion to an adherend (for example, artificial joint), etc., the cumulative ratio of power particles having aspect ratios of 1.00 or more and less than 1.10 in all of the powder particles contained in the composition for hard tissue repair (the sum of the polymer powder (B) and other powder particles corresponds to 100 cumulative %) is 75 cumulative % or less, preferably 70 cumulative % or less, more preferably 2.5 to 65 cumulative %, and more preferably 3.0 to 60 cumulative %. It is preferable to define the cumulative ratio of the powder particles having aspect ratios of 1.00 or more and less than 1.10, as such a specific ratio or more as described above from a viewpoint of suppression of remarkable thickening to enable to prepare a homogeneous composition for hard tissue repair; suppression of decrease in the anchoring effect with substantial reduction of the contact area with an adherend; and improvement of various properties such as adhesion to an adherend (e.g., artificial joint), etc. In addition, it is preferable to define the cumulative ratio of powder particles having aspect ratios of 1.00 or more and less than 1.10, as such a specific ratio or less as described above from a viewpoint of appropriately keeping of the solubility of the polymer powder (B) in the monomer (A); expression of the sufficient thickening effect and cage effect ("Trommsdorff effect"); shortening of the dough time; and improvement of various properties such as operability of the composition for hard tissue repair, etc.

Further, regarding various properties such as penetrability into an adherend (for example, cancellous bone), etc., the cumulative ratio of power particles having aspect ratios of 1.00 or more and less than 1.10 to all of the powder particles contained in the composition for hard tissue repair (the sum of the polymer powder (B) and other powder particles corresponds to 100 cumulative %) is 75 cumulative % or less, preferably 2.5 to 55 cumulative %, more preferably 3.0 to 40 cumulative %, and more preferably 3.0 to 35 cumulative %. It is preferable to define the cumulative ratio of the powder particles having aspect ratios of 1.00 or more and less than 1.10 as such a specific ratio or more as described above from a view point of suppression of remarkable thickening, and improvement of various properties such as penetrability into an adherend (e.g., cancellous bone), etc. In addition, it is preferable to define the cumulative ratio of the powder particles having aspect ratios of 1.00 or more and less than 1.10 as such a specific ratio or less as described above from a viewpoint of suppression of dilatancy expression, and improvement of various properties such as penetrability into an adherend (e.g., cancellous bone), etc.

Regarding various properties such as reduction of the amount of eluted monomers, etc., the cumulative ratio of power particles having aspect ratios of 1.00 or more and less than 1.10 to all of the powder particles contained in the composition for hard tissue repair (the sum of the polymer powder (B) and other powder particles corresponds to 100 cumulative %) is 75 cumulative % or less, preferably 70 cumulative % or less, more preferably 2.5 to 65 cumulative %, more preferably 2.5 to 55 cumulative %, more preferably 4.0 to 40 cumulative %, and more preferably 4.0 to 35 cumulative %. It is preferable to define the cumulative ratio of the powder particles having aspect ratios of 1.00 or more and less than 1.10, as such a specific ratio or more as described above from a viewpoint of suppression of remarkable thickening to enable to prepare of a homogeneous composition for hard tissue repair; suppression of increase of the ununiform structures on the surface and/or inside of the cured product; and improvement of various properties such as reduction of the amount of eluted monomers, etc. In addition, it is preferable to define the cumulative ratio of the polymer powder particles (B-y) having such a small aspect ratio, as such a specific ratio or less as described above from a viewpoint of expression of the sufficient cage effect ("Trommsdorff effect"), and improvement of various properties such as reduction of the amount of eluted monomers, etc.

The aspect ratio of the polymer powder (B-x) is 1.10 or more. From the standpoint of improvement of various properties required for the composition for hard tissue repair, the above aspect ratio is preferably 1.10 or more and 1.90 or less; and more preferably 1.15 or more and 1.80 or less. It is preferable to define the aspect ratio of the polymer powder (B-x) as such a specific ratio or more as described above from a viewpoint of, for example, easy expression of the desired solubility of the polymer powder (B-x) in the monomer (A) and improvement of various properties. In addition, it is preferable to define the aspect ratio of the polymer powder (B-x) as such a specific ratio or less as described above from a viewpoint of, for example, suppression of excessive increase in the solubility of the polymer powder (B-x) in the monomer (A) over the desired level, or suppression of an excessive increase in the aggregability of the polymer powder (B) or the whole powder particles; which result in improvement of various properties such as the operability of the composition for hard tissue repair, etc.

The aspect ratio of the polymer powder (B-y) is 1 or more and less than 1.10. From the standpoint of improving various properties required for the composition for hard tissue repair, the above aspect ratio is preferably 1.00 or more and 1.05 or less. It is preferable to define the aspect ratio of the polymer powder (B-y) as 1.05 or less as described above from a viewpoint of, for example, suppression of excessive increase in the solubility of the polymer powder (B-y) in the monomer (A) over the desired level, or suppression of excessive increase in the aggregability of the polymer powder (B) or the whole powder particles, which result in improvement of various properties such as the operability of the composition for hard tissue repair, etc.

When the polymer powder (B) contains the polymer powder (B-x) and the polymer powder (B-y), the aspect ratio of the whole polymer powder (B) is preferably 1.11 or more and 1.80 or less, more preferably 1.15 or more and 1.80 or less, and more preferably 1.15 or more and 1.75 or less, from the viewpoint of improving various properties required for the composition for hard tissue repair. It is preferable to define the aspect ratio of the whole polymer powder (B) within such a specific range as described above from a viewpoint of, for example, keeping of the solubility of the polymer powder (B) in the monomer (A) at an appropriate level, or keeping of the aggregability of the polymer powder (B) or the whole powder particles at an appropriate level, which result in improvement of various properties such as the operability of the composition for hard tissue repair, etc.

The measuring methods of the aspect ratio and the cumulative ratio (%) explained as above are described in the section of Examples described later.

The weight average molecular weight of the polymer powder (B) (when one kind of polymer is used alone as a single component, the weight average molecular weight of the polymer used alone is adopted, while, when a mixture of two or more kinds of polymers is used, the weight average molecular weight of the entire mixture is adopted) is preferably from 40,000 to 6,000,000, more preferably from 50,000 to 5,000,000, more preferably from 75,000 to 2,000,000, more preferably from 75,000 to 880,000, and more preferably from 100,000 to 400,000, from the viewpoint of improving various properties required for the composition for hard tissue repair. It is preferable to define the weight average molecular weight of the polymer powder (B) within such a specific range as described above from a viewpoint of, for example, keeping of the solubility of the polymer powder (B) in the monomer (A) at an appropriate level and suppression of the thickening effect and cage effect ("Trommsdorff effect"), which result in improvement of the operability of the composition for hard tissue repair. Moreover, when the operability is improved, it becomes easier to obtain a composition for hard tissue repair having excellent homogeneity. As a result, various properties tend to be improved, which properties include adhesion to an adherend, penetrability into an adherend, reduction of the amount of eluted monomers, as well as, regarding the composition for hard tissue repair after curing, flexural modulus, tensile strength, compressive strength, flexural strength, toughness (surface dissipation energy limit value), etc.

The volume mean particle diameter of the polymer powder (B) (when one kind of polymer powder is used alone as a single component, the volume mean particle diameter of the polymer powder used alone is adopted, while, when a mixture of two or more kinds of polymer powders is used, the volume mean particle diameter of the entire mixture is adopted) is preferably 7 to 120 µm, more preferably 10 to 118 µm, and more preferably 15 to 77 µm, from the viewpoint of improving various properties required for the composition for hard tissue repair. It is preferable to define the volume mean particle diameter of the polymer powder (B) within such a specific range as described above from a viewpoint of, for example, keeping of the solubility of the polymer powder (B) in the monomer (A) at an appropriate level and suppression of the thickening effect and cage effect ("Trommsdorff effect"), which result in improvement of the operability of the composition for hard tissue repair. Moreover, when the operability is improved, it becomes easier to obtain a composition for hard tissue repair having excellent homogeneity. As a result, various properties tend to be improved, which properties include adhesion to an adherend, penetrability into an adherend, reduction of the amount of eluted monomers, as well as, regarding the composition for hard tissue repair after curing, flexural modulus, tensile strength, compressive strength, flexural strength, toughness (surface dissipation energy limit value), etc.

The blending amount of the polymer powder (B) is preferably 54.9 to 80 parts by mass, more preferably 56.7 to 73.7 parts by mass, and further preferably 59.7 to 70.7 parts by mass (the sum of the components (A) to (C) is taken as 100 parts by mass), from the viewpoint of improving various properties required for the composition for hard tissue repair. It is preferable to define the blending amount of the polymer powder (B) within such a specific range as described above from a viewpoint of, for example, keeping of the solubility of the polymer powder (B) in the monomer (A) at an appropriate level and suppression of the thickening effect and cage effect ("Trommsdorff effect"), which result in improvement of the operability of the composition for hard tissue repair. Moreover, when the operability is improved, it becomes easier to obtain a composition for hard tissue repair having excellent homogeneity. As a result, various properties tend to be improved, which properties include adhesion to an adherend, penetrability into an adherend, reduction of the amount of eluted monomers, as well as , regarding the composition for hard tissue repair after curing, flexural modulus, tensile strength, compressive strength, flexural strength, toughness (surface dissipation energy limit value), etc.

[Polymerization Initiator (C)]

The polymerization initiator (C) used in the present invention is not particularly limited, and various known compounds can be used. Among them, an organic boron compound (c1) and an organic peroxide are preferable, and the organic boron compound (c1) is more preferable. The organic boron compound (c1) is likely to shorten the dough time as compared with other polymerization initiators. The reason for this is considered to be that the polymerization reaction proceeds from the interface with the surrounding air directly contacting the composition for hard tissue repair, which becomes a soft mass (dough) form by disappearing the stringiness at an early stage. Furthermore, it is also considered as the reason that, even if the composition for hard tissue repair contains water, the polymerization activity is increased or maintained by the dissolved oxygen in water.

The organic peroxide includes, for example, diacyl peroxides such as diacetyl peroxide, diisobutyl peroxide, didecanoyl peroxide, benzoyl peroxide (BPO) and succinic acid peroxide, etc.; peroxydicarbonates such as diisopropylperoxydicarbonate, di-2-ethylhexylperoxydicarbonate, diallylperoxydicarbonate, etc.; peroxyesters such as tert-butylperoxy isobutyrate, tert-butyl peroxy neodecanate, cumene peroxy neodecanate, etc.; and peroxy sulfonates such as acetylcyclohexylsulfonyl peroxide, etc.

The organic peroxide may be used as a redox initiator in combination with a tertiary amine or with a tertiary amine and either sulfinic acid or its alkali metal salt. Among them, benzoyl peroxide (BPO) combined with N,N-dimethyl-p-toluidine, and, benzoyl peroxide (BPO) combined with N,N-dihydroxyethyl-p-toluidine, are preferably used.

The tertiary amine, etc., such as N,N-dimethyl-p-toluidine, N, N-dihydroxyethyl-p-toluidine are preferably added to the monomer (A) prior to use. The addition amount thereof is preferably 5.0 parts by mass or less, more preferably 0.1 to 3.0 parts by mass, and more preferably 0.25 to 2.6 parts by mass (the sum of the monomer (A) and the tertiary amine is taken as 100 parts by mass). When the tertiary amine is used, the polymerization reaction can be initiated easily without heating, because radicals are generated by electron transfer even at room temperature.

As the organic boron compound (c1), for example, trialkylboron, alkoxyalkylboron, dialkylborane, partially oxidized trialkylboron and alkylborane-amine complex can be used.

Concrete examples of the trialkylboron include trialkylborons including an alkyl group(s) having 2 to 8 carbon atoms such as triethylboron, tripropylboron, triisopropylboron, tributylboron, tri-sec-butylboron, triisobutylboron, tripentylboron, trihexylboron, triheptylboron, trioctylboron, tricyclopentylboron, tricyclohexylboron, etc. The alkyl group may be any one of a linear alkyl group, a branched alkyl group or a cycloalkyl group, and three alkyl groups contained in trialkylboron may be the same or different each other.

Concrete examples of the alkoxyalkylboron include monoalkoxydialkylborons such as butoxydibutylboron, etc.; and dialkoxymonoalkylborons. The alkyl group of the alkoxyalkylboron and the alkyl portion of its alkoxy group may be the same or different each other.

Concrete examples of the dialkylborane include dicyclohexylborane and diisoamylborane. Two alkyl groups of the dialkylborane may be the same or different. Two alkyl groups contained in the dialkylborane may be connected to form a monocyclic structure or a bicyclo structure. Such compounds include, for example, 9-borabicyclo [3.3.1] nonane.

The partially oxidized trialkylboron is a partial oxide compound of a trialkylboron. Among them, partially oxidized tributylboron is preferable. The amount of oxygen to be added with respect to 1 mol of a trialkylboron is preferably 0.3 to 0.9 mol, more preferably 0.4 to 0.6 mol.

Concrete examples of the alkylborane-amine complexes include triethylborane-diaminopropane (TEB-DAP), triethylborane-diethylenetriamine (TEB-DETA), tri-n-butylborane-3-methoxypropylamine (TnBB-MOPA), tri-n-butylbotane-diaminopropane (TnBB-DAP), tri-sec-butylborane-diaminopropane (TsBB-DAP), methylaminoethoxydiethylborane (MAEDEB), methylaminoethoxydicyclohexylborane (MAEDCB) and derivatives derived therefrom. One of these alkylborane-amine complexes can be used alone, or two or more complexes can be used in combination.

When the alkylborane-amine complex is used as the polymerization initiator (C), it is preferred to additionally use a decomplexing agent together with the monomer (A). The term "decomplexing agent" used in the specification means a compound which is capable of releasing an alkylborane from the alkylborane-amine complex, and permits the initiation of the polymerization reaction by release of the alkylborane.

As a suitable decomplexing agent, for example, any acids, or acidic group-containing monomer(s) (the above-mentioned acidic group-containing monomer(s) used as the monomer (A)) can be used. Preferred acids include Lewis acids (e.g., $SnCl_4$, $TiCl_4$) and Broensted acids (e.g., carboxylic acids, HCl, $H_2SO_4$, $H_3PO_4$, phosphonic acid, phosphinic acid, silicic acid). Suitable carboxylic acids include those represented by the general formula R—COOH. In the formula, R represents a hydrogen atom, an alkyl group having 1 to 8 carbon atoms (preferably an alkyl group having 1 to 4 carbon atoms), an alkenyl group having 2 to 8 carbon atoms (preferably an alkenyl group having 2 to 4 carbon atoms), an alkynyl group having 2 to 8 carbon atoms (preferably an alkynyl group having 2 to 4 carbon atoms), or an aryl group having 6 to 10 carbon atoms (preferably an aryl group having 6 to 8 carbon atoms). The alkyl group, the alkenyl group and the alkynyl group represented by R may be linear or branched. The aliphatic group in R may be saturated or unsaturated. The aryl group in R may be substituted with a substituent(s) such as an alkyl group, an alkoxy group, a halogen atom, etc., or may be un-substituted. Concrete examples of the acid as the carboxylic acid represented by the above-described general formula include acrylic acid, methacrylic acid, acetic acid, benzoic acid and p-methoxybenzoic acid. Specific examples of the acidic group-containing monomer(s) are those as described in the section of the monomer (A) mentioned above, among them, 4-methacryloxyethyltrimellitic acid and an anhydride thereof are preferable.

Among the organic boron compounds (c1), tributylboron and partially oxidized tributylboron are preferred, and partially oxidized tributylboron is more preferable. When tributylboron and/or partially oxidized tributylboron are used as the organic boron compound (c1), not only the operability is improved, but also there is tendency to provide appropriate reactivity to a living organism containing water. In addition, when tributylboron and/or partially oxidized tributylboron are used as the organic boron compound (c1), the reaction starts even at a place with a large amount of water such as living organisms, and the reaction proceeds. As a result, the monomers rarely remain at the interface between the composition and the living organism, and harm against the living organism in such situation is extremely little. One of these organic boron compounds (c1) can be used alone, or two or more organic boron compounds (c1) can be used in combination.

The organic boron compound (c1) may further contain an aprotic solvent. When the organic boron compound (c1) is diluted with an aprotic solvent, the heat buildup of the pyrophoric organic boron compound (c1) becomes milder, and its pyrophoricity is suppressed, and, then, the handling during transport, storage and mixing treatment becomes easier. Further, since rapid heat generation can be suppressed, even when a very large amount of a composition for hard tissue repair is used, damage to the tissue in contact with the composition for hard tissue repair tends to be reduced. The boiling point at one atmosphere pressure (1 atm) of the aprotic solvent is usually 30° C. to 150° C., preferably 50° C. to 120° C. It is preferable to define the boiling point of the aprotic solvent as such a specific temperature or higher as described above from a viewpoint of suppression of volatilization or scattering of the aprotic solvent from the polymerization initiator during transportation or storage; and sufficient suppression of the heat generation and ignition property of the organic boron compound (c1). In addition, it is preferable to define the boiling point of the aprotic solvent as such a specific temperature or lower as described above from a viewpoint of reduction of the residual amount of the aprotic solvent in the cured product obtained from the composition for hard tissue repair, and improvement of various properties of the cured product such as adhesive strength to an affected site and flexural modulus, as well as, tensile strength, compressive strength, flexural strength, etc.

As the aprotic solvents, such solvents are preferable, which have no groups comprising an active hydrogen such as a hydroxy group, a mercapto group, etc., reacting with an organic boron compound (c1), and which can form a homogeneous solution with the organic boron compound (c1).

Examples of the aprotic solvent include hydrocarbons such as pentane, hexane, cyclohexane, heptane, benzene, toluene, etc.; halogenated hydrocarbons such as fluorobenzene, 1,1-dichloroethane, 1,2-dichloroethane, so-called flon, i.e., fluorocarbon, etc.; ethers such as diethyl ether, diisopropyl ether, ethylene glycol dimethyl ether, tetrahydrofuran, etc.; ketones such as acetone, methyl ethyl ketone, diethyl ketone, etc.; and esters such as methyl acetate, ethyl acetate, isopropyl acetate, etc. Among them, saturated aliphatic hydrocarbons such as pentane, hexane, heptane, etc., ethers and esters are preferable. Hexane, diisopropyl ether and ethyl acetate are more preferable. One of these aprotic solvents can be used alone, or two or more aprotic solvents can be used in combination.

The content of the aprotic solvent is preferably 30 to 80 parts by mass with respect to 100 parts by mass of the organic boron compound (c1). It is preferable to define the content of the aprotic solvent as such a specific temperature or higher as described above from a viewpoint of sufficient dilution of the organic boron compound (c1), and sufficient suppression of the heat generation and ignition property of the organic boron compound (c1). In addition, it is preferable to define the content of the aprotic solvent as such a specific temperature or lower as described above from a viewpoint of suppression of decrease in the polymerization initiation ability of the organic boron compound (c1).

The organic boron compound (c1) may contain an alcohol in addition to or in place of the aprotic solvent. By adding an alcohol to the organic boron compound (c1), there is a tendency that the reaction by the organic boron compound (c1) becomes further milder without reducing the polymerization activity, and burning and firing are easily suppressed even when the organic boron compound (c1) comes into contact with a material such as paper, etc., in the air.

The boiling point of the alcohol at 1 atm is usually 60° C. to 180° C., preferably 60° C. to 120° C. It is preferable to define the boiling point of the alcohol as such a specific temperature or higher as described above from a viewpoint of suppression of volatilization or scattering of the alcohol from the polymerization initiator during transportation or during storage, and sufficient suppression of the heat generation and ignition property of the organic boron compound (c1). In addition, it is preferable to define the boiling point of the alcohol as such a specific temperature or lower as described above from a viewpoint of reduction of the residual amount of the alcohol in the cured product obtained from the composition for hard tissue repair, and improvement of various properties of the cured product such as adhesive strength to an affected site and flexural modulus, as well as, tensile strength, compressive strength, flexural strength, etc.

The alcohol includes, for example, methanol, ethanol, n-propanol and isomers thereof, n-butanol and isomers thereof, n-pentanol and isomers thereof, n-hexanol and isomers thereof, and n-heptanol and isomers thereof. Among them, alcohols having 4 or less carbon atoms, i.e., methanol, ethanol, n-propanol and isomers thereof, and n-butanol and isomers thereof are preferable, and ethanol and n-propanol are more preferable. One of these alcohols can be used alone, or two or more alcohols can be used in combination.

The content of the alcohol is usually 0.01 to 40 parts by mass, preferably 0.1 to 30 parts by mass, and more preferably 0.5 to 20 parts by mass with respect to 100 parts by mass of the organic boron compound (c1).

When an alcohol and an aprotic solvent are used in combination, the content of the aprotic solvent is desirably 5 to 40 parts by mass, preferably 10 to 30 parts by mass, and more preferably 10 to 25 parts by mass with respect to 100 parts by mass of the organic boron compound (c1).

The blending amount of the polymerization initiator (C) is preferably 0.1 to 10 parts by mass, more preferably 1.0 to 7.0 parts by mass, and more preferably 2.1 to 4.3 parts by mass with respect to 100 parts by mass of the sum of the monomer (A), the polymer powder (B) and the polymerization initiator (C). When the blending amount of the polymerization initiator (C) is the set value or more as described above, such blending amount is preferable from the viewpoint that safety to the living tissue can be easily ensured, because it is possible to reduce the unpolymerized components as the monomer (A) remaining in and/or eluted from the composition by expression of the desired polymerization initiation ability of the polymerization initiator. In addition, when the blending amount is the set value or less as described above, such blending amount is preferable from the viewpoint that rapid formation of a polymerized hard product can be prevented by suppressing rapid polymerization progress and/or heat generation. Further, the polymerization initiator (C) in liquid form is preferable from the viewpoint that decrease of handling performance due to excessive viscosity reduction can be suppressed.

[Contrast Medium (X)]

The composition for hard tissue repair according to the present invention may contain a contrast medium (X). The volume mean particle diameter of the contrast medium (X) is preferably 0.15 to 25.1 μm, and more preferably 0.45 to 18.0 μm. It is preferable that the volume mean particle diameter of the contrast medium (X) is within such a certain range as described above, from a viewpoint that the desired handling property of the composition for hard tissue repair can be easily expressed by keeping an appropriate aggregability of the contrast medium (X) and/or the whole powder particle (as the sum of the polymer powder (B) and other powder particles is 100 cumulative %).

The type of the contrast medium (X) is not particularly limited, and includes barium sulfate, zirconia, bismuth carbonate, calcium tungstate, ytterbium, and iodine compounds. Of these, barium sulfate and zirconia are preferable, because they have a proven record in their uses for hard tissue, in particular, as a bone cement.

The blending amount of the contrast medium (X) is preferably 0 to 70 parts by mass, more preferably 0.01 to 70 parts by mass, more preferably 0.01 to 45 parts by mass, more preferably 2.5 to 33.8 parts by mass, and more preferably 4.5 to 22.5 parts by mass with respect to 100 parts by mass of the sum of the monomer (A), the polymer powder (B) and the polymerization initiator (C).

[Antimicrobial Drug Particle (Y)]

The composition for hard tissue repair of the present invention may contain antimicrobial drug particles (Y). Concrete examples of the antimicrobial drug include antibiotics, elemental iodine, solid polyvinylpyrrolidone iodine and polyvinylpyrrolidone iodine; phenol compounds such as tribromophenol, trichlorophenol, tetrachlorophenol, nitrophenol, 3-methyl-4-chlorophenol, 3,5-dimethyl-4-chlorophenol, phenoxyethanol, dichlorophen, o-phenylphenol, m-phenylphenol, p-phenylphenol, 2-benzyl-4-chlorophenol, 2,4-dichloro-3,5-dimethylphenol, 4-chlorothymol, chlorphen, triclosan, fenticlor, phenol, 2-methylphenol, 3-methylphenol, 4-methylphenol, 4-ethylphenol, 2,4-dimethylphenol, 2,5-dimethylphenol, 3,4-dimethylphenol, 2,6-dimethylphenol, 4-n-propylphenol, 4-n-butylphenol, 4-n-amylphenol, 4-tert-amylphenol, 4-n-hexylphenol, 4-n-heptylphenol, monoalkylhalophenols, polyalkylhalophenols, aromatic halophenols, and ammonium salts, alkali metal salts and alkaline earth metal salts thereof; silver nitrate; hexachlorophene; and merbromin. Of these, antibiotics are preferable.

Among the substances produced by microorganisms or chemically synthesized, the antibiotics mean those inhibiting the growth of the other microorganisms. In addition, the definition of the antibiotics also includes those obtained by chemical conversion of microbial products or chemical synthesis.

Concrete examples of the antibiotics include gentamicin, gentamicin sulfate, tobramycin, tobramycin sulfate, am ikacin, am ikacin sulfate, dibekacin, dibekacin sulfate, vancomycin, vancomycin hydrochloride, daptomycin, arbekacin, arbekacin sulfate, fosfomycin, cefazolin, cefazolin sodium, minocycline, clindamycin, colistin, linezolid, tetracycline hydrochloride, tetracycline hydrate, oxytetracycline and erythromycin. Of them, it is preferable to contain at least one antibiotic selected from the group consisting of gentamicin, tobramycin, amikacin, dibekacin, vancomycin, daptomycin, and pharmacologically acceptable salts thereof.

When daptomycin or a pharmacologically acceptable salt thereof are used as the antimicrobial drug particles (Y), it is particularly desirable to use it together with a filler having a property for sustained-release of calcium among the inorganic fillers described below. A daptomycin derivative bound to calcium in the elemental from or calcium ion penetrates into the cell membranes of bacteria and binds thereto, and, thus, depolarization of the cell membranes progresses. Such progress makes the cells to go into death by subjecting the cells to lose their membrane potential. Therefore, there is a tendency that its antimicrobial activity improves. One of the fillers with the sustained-release of calcium can be used alone or two or more fillers can be used in combination.

The volume mean particle diameter of the antimicrobial agent particles (Y) is preferably less than 250 μm, more preferably 1.0 to 200 μm, and more preferably 2.5 to 150 μm.

The amount of the antimicrobial drug particles (Y) to be blended may be appropriately determined according to the type. Its amount is preferably 30 parts by mass or less, more preferably 0.01 to 30 parts by mass, more preferably 1.0 to 30 parts by mass, more preferably 1.2 to 25 parts by mass, and more preferably 1.4 to 20 parts by mass with respect to 100 parts by mass of the sum of the monomer (A), the polymer powder (B) and the polymerization initiator (C).

[Polysaccharides (Z)]

The composition for hard tissue repair of the present invention may contain a polysaccharide (Z). Concrete examples of the polysaccharides (Z) include sucrose, lactose, maltose, trehalose, turanose, cellobiose, raffinose, melezitose, maltotriose, acarbose, stachyose, starch, glycogen, cellulose, carboxymethylcellulose, dextrin, glucan, xyloglucan, fructan, chitin, chitosan, agarose, carrageenan, hyaluronic acid, pectin, glucomannan, chondroitin sulfate, alginic acid, pullulan, and derivatives and/or pharmacologically acceptable salts derived therefrom. One of these polysaccharides can be used alone or two or more thereof can be used in combination. In particular, when it is used together with the above-mentioned antimicrobial drug particles (Y) and/or fillers having the sustained-release property of calcium described below, there are a tendency of improving the antimicrobial property and/or a tendency of reducing harm to the living body.

The blending amount of the polysaccharide (Z) may be appropriately determined depending on its type. The blending amount is preferably 40 parts by mass or less, and more preferably 0.1 to 30 parts by mass with respect to 100 parts by mass of the sum of the monomer (A), the polymer powder (B) and the polymerization initiator (C).

[Other Components]

The composition for hard tissue repair of the present invention may contain a polymerization inhibitor, if necessary. The polymerization inhibitors includes hydroquinone compounds such as hydroquinone, dibutyl hydroquinone, etc.; phenols such as hydroquinone monomethyl ether, 2,6-di-tert-butylphenol, 2,6-di-tert-butyl-p-cresol, etc.; catechol; pyrogallol; benzoquinone; 2-hydroxybenzoquinone; p-methoxyphenol; t-butylcatechol; butylated hydroxy anisole; butylated hydroxytoluene; t-butylhydroquinone, etc. Among them, a mixture of hydroquinone monomethyl ether and 2,6-di-tert-butyl-p-cresol is preferable. In addition, hydroquinone monomethyl ether may be preferable in terms of its own stability in some cases. One of the polymerization inhibitors can be used alone or, two or more polymerization inhibitors can be used in combination.

The amount of the polymerization inhibitor to be added is preferably 1 to 1500 ppm, more preferably 5 to 1000 ppm, and more preferably 5 to 500 ppm, based on the entire amount of the composition for hard tissue repair. The addition amount of the polymerization inhibitor is 10 to 5000 ppm, more preferably 25 to 1000 ppm, and more preferably 25 to 500 ppm with respect to the monomer (A).

The composition for hard tissue repair of the present invention may contain an ultraviolet absorber, if necessary.

Concrete examples of the ultraviolet absorbers include:

benzotriazole compounds such as 2-(2'-hydroxy-5'-methylphenyl) benzotriazole, 2-(3',5'-di-tert-butyl-2'-hydroxyphenyl) benzotriazole, 2-(5'-tert-butyl-2'-hydroxyphenyl) benzotriazole, 2-(2'-hydroxy-5'-(1,1,3,3-tetramethylbutyl) phenyl) benzotriazole, 2-(3',5'-di-tert-butyl-2'-hydroxyphenyl)-5-chloro-benzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3',5'-di-tert-amyl-2'-hydroxyphenyl) benzotriazole, 2-(3',5'-bis(α,α-dimethylbenzyl)-2'-hydroxyphenyl) benzotriazole, 2-(3'-tert-butyl-2'-hydroxy-5'-(2-octyloxycarbonylethyl) phenyl)-5-chlorobenzotriazole, 2-(3'-tert-butyl-5'-[2-(2-ethylhexyloxy) carbonylethyl]-2'-hydroxyphenyl)-5-chlorobenzotriazole, 2-(3'-tert-butyl-2'-hydroxy-5'-(2-methoxycarbonylethyl) phenyl)-5-chlorobenzotriazole, 2-(3'-tert-butyl-2'-hydroxy-5'-(2-methoxycarbonylethyl) phenyl) benzotriazole, 2-(3'-tert-butyl-2'-hydroxy-5'-(2-octyloxycarbonylethyl) phenyl) benzotriazole, 2-(3'-tert-butyl-5-[2-(2-ethylhexyloxy) carbonylethyl]-2'-hydroxyphenyl) benzotriazole, 2-(3'-dodecyl-2'-hydroxy-5'-methylphenyl) benzotriazole, a mixture of 2-(3'-tert-butyl-2'-hydroxy-5'-(2-isooctyloxycarbonylethyl) phenyl) benzotriazole and 2,2'-methylene-bis[4-(1,1,3,3-tetramethylbutyl)-6-benzotriazol-2-ylphenol], a transesterification reaction product of 2-[3'-tert-butyl-5'-(2-m ethoxycarbonylethyl)-2'-hydroxyphenyl] benzotriazole with polyethylene glycol 300, [[R—CH$_2$CH$_2$—COOCH$_2$]$_3$]$_2$— (wherein, R=3'-tert-butyl-4'-hydroxy-5'-2H-benzotriazol-2-yl-phenyl), etc.;

benzophenone compounds such as 2,4-dihydroxybenzophenone, 2-hydroxy-4-methoxybenzophenone, 2-hydroxy-4-octoxybenzophenone, 2-hydroxy-4-decyloxybenzophenone, 2-hydroxy-4-dodecyloxybenzophenone, 2-hydroxy-4-benzyloxybenzophenone, 2,2',4,4'-tetrahydroxybenzophenone, 2,2'-dihydroxy-4,4'-dimethoxybenzophenone, etc.;

4-tert-butylphenyl salicylate, phenyl salicylate, octylphenyl salicylate, dibenzoylresorcinol, bis(4-tert-butylbenzoyl)

resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl benzoate, and 3,5-di-tert-butyl-4-hydroxybenzoate;

hindered amine compounds such as bis (2,2,6,6-tetramethyl piperidyl) sebacate, bis (2,2,6,6-tetramethyl piperidyl) succinate, bis (1,2,2,6,6-pentamethyl piperidyl) sebacate, bis (1,2,2,6,6-pentamethyl piperidyl) n-butyl-3,5-di-tert-butyl-4-hydroxybenzyl malonate, a condensation product of 1-hydroxyethyl-2,2,6,6-tetramethyl-4-hydroxypiperidine with succinic acid, a condensation product of N,N'-bis-(2,2,6,6-tetramethyl-4-piperidyl) hexamethylenediamine with 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl)-1,2,3,4-butane tetraoate, 1,1'-(1,2-ethanediyl) bis (3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethyl-4-piperidyl) 2-n-butyl-2-(2-hydroxy-3,5-di-tert-butylbenzyl) malonate, 3-n-octyl-7,7,9,9-tetramethyl-1,3,8-triazaspiro [4.5] decane-2,4-dione, bis (1-octyloxy-2,2,6,6-tetramethyl piperidyl) sebacate, bis (1-octyloxy-2,2,6,6-tetramethylpiperidyl) succinate, a condensation product of N,N'-bis (2,2,6,6-tetramethyl-4-piperidyl) hexamethylenediamine with 4-morpholino-2,6-dichloro-1,3,5-triazine, a condensation production of 2-chloro-4,6-di-(4-n-butylamino-2,2,6,6-tetramethylpiperidyl)-1,3,5-triazine and 1,2-bis (3-aminopropylamino) ethane, a condensation product of 2-chloro-4,6-di-(4-n-butylamino-1,2,2,6,6-pentamethylpiperidyl)-1,3,5-triazine with 1,2-bis (3-aminopropylamino) ethane, 8-acetyl-3-dodecyl-7,7,9,9-tetramethyl-1,3,8-triazaspiro [4.5] decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl) pyrrolidine-2,5-dione etc.;

oxalamide compounds such as 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis (3-dimethylaminopropyl) oxalamide, a mixture of 2-ethoxy-5-tert-butyl-2'-ethyloxanilide and 2-ethoxy-2'-ethyl-5,4'-di-tert-butyloxanilide, mixtures of o- and p-methoxy, and o- and p-ethoxy-disubstituted oxalinide, etc.;

2-(2-hydroxyphenyl)-1,3,5-triazine compounds such as 2,4,6-tris (2-hydroxy-4-octyloxyphenyl)-1,3,5-triazine, 2-(2-hydroxy-4-octyloxyphenyl)-4,6-bis (2,4-dimethylphenyl)-1,3,5-triazine, 2-(2,4-dihydroxyphenyl)-4,6-bis (2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl) -4,6-bis (4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2-hydroxy-3-butyloxypropyloxy) phenyl]-4,6-bis (2,4-dimethylphenyl)-1,3,5-triazine, 2-[2-hydroxy-4-(2-hydroxy-3-octyloxypropyloxy) phenyl]-4,6-bis (2,4-dimethylphenyl)-1,3,5-triazine, 2-[4-dodecyl/tridecyloxy-(2-hydroxypropyl) oxy-2-hydroxyphenyl]-4,6-bis (2,4-dimethylphenyl)-1,3,5-triazine etc.;
and phosphite compounds or phosphonite compounds such as triphenyl phosphite, diphenyl alkyl phosphite, phenyl dialkyl phosphite, tris (nonylphenyl phosphite), trilauryl phosphite, trioctadecyl phosphite, distearyl pentaerythrityl diphosphite, tris-(2,4-di-tert-butylphenyl) phosphite, diisodecylpentaerythrityl diphosphite, bis (2,4-di-tert-butylphenyl) pentaerythrityl diphosphite, bis (2,6-di-tert-butyl-4-methylphenyl) pentaerythrityl diphosphite, bis-isodecyloxypentaerythrityl diphosphite, bis (2,4-di-tert-butyl-6-methylphenyl) pentaerythrityl diphosphite, bis (2,4,6-tri-tert-butylphenyl) pentaerythrityl diphosphite, tristearylsorbityl triphosphate, tetrakis (2,4-di-tert-butylphenyl) 4,4'-biphenylene diphosphonite, 6-isooctyloxy-2,4,8,10-tetra-tert-butyl-12H-dibenzo [d,g]-1,3,2-dioxaphosphocin, 6-fluoro-2,4,8,10-tetra-tert-butyl-12H-methyldibenzo [d,g]-1,3,2-dioxaphosphocine, bis (2,4-di-tert-butyl-6-methylphenyl) methyl phosphite, bis (2,4-di-tert-butyl-6-methylphenyl) ethyl phosphite etc.

Among them, benzotriazole compounds are preferable.

The amount of the ultraviolet absorber to be added is preferably 1000 ppm or less, more preferably 800 ppm or less, and more preferably 500 ppm or less with respect to the monomer (A). The coloring of the liquid containing the monomer is suppressed, and the storage stability of the monomer itself tends to be improved by adding the ultraviolet absorber in such amounts.

Examples of other components further include softeners and plasticizers.

Examples of the softeners include rubbers such as natural rubber, synthetic rubber, etc., and elastomers such as thermoplastic elastomers, etc. Such softeners can enhance the softness of the composition for hard tissue repair. Examples of the synthetic rubber include EPT (ethylene-propylene terpolymer). Examples of the thermoplastic elastomer include styrene-based elastomers, vinyl chloride-based elastomers, olefin-based elastomers, polyester-based elastomers, polyimide-based elastomers and urethane-based elastomers. The molecular weight of the elastomer is usually 1000 to 1,000,000, and preferably 2000 to 500,000. The glass transition point (Tg) of the elastomer described above is usually 20° C. or less, and preferably 0° C. or less.

Examples of the plasticizers include hydroxycarboxylic acid esters such as esters of citric acid, esters of isocitric acid, esters of tartaric acid, esters of malic acid, esters of lactic acid, esters of glyceric acid, esters of glycolic acid, etc.; trimethyl trimellitate, diethylene glycol dibenzoate, diethyl malonate, triethyl O-acetyl citrate, benzylbutyl phthalate, dipropylene glycol dibenzoate, diethyl adipate, tributyl O-acetyl citrate, dimethyl sebacate and alkylene glycol diesters.

The addition amount of the softener and the plasticizer may be appropriately determined depending on the type thereof. The amount thereof is generally 0 to 30% by mass, preferably 0 to 20% by mass, and more preferably 0 to 10% by mass in the whole composition for hard tissue repair.

Examples of the other components include further a preservative. Concrete examples of the preservative include methylparaben, methylparaben sodium, ethylparaben, propylparaben, propylparaben sodium, butylparaben; cresol, chlorocresol; resorcinol, 4-n-hexylresorcinol, 3a,4,7,7a-tetrahydro-2-[(trichloromethyl)thio)]-1H-isoindole-1,3 (2H)-dione; benzalkonium chloride, benzalkonium sodium chloride, benzethonium chloride; benzoic acid, benzyl alcohol, cetylpyridinium chloride, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, phenylmercury compounds such as phenylmercuric borate, phenylmercuric nitrate, phenylmercuric acetate, etc., and formaldehyde.

Examples of the other components further include analgesics, a composition containing an analgesic, anorectic drugs, antihelmintic drugs, antiarthritic agents, antiasthmatic drugs, anticonvulsants, antidepressant agents, antidiuretics, antidiarrheal agents, antihistamine drugs, anti-inflammatory drugs, antimigraine drugs, antiemetic agents, antineoplasm drugs, antiparkinsonian agents, antipruritic drugs, antipsychotics, antipyretic drugs, antispasmodic drugs, anticholinergic agents, sympathomimetic agents, cardiovascular drugs, antiarrhythmic drugs, antihypertensive drugs, diuretics, vasodilators, immunosuppressant drugs, muscle-relaxant drugs, parasympatholytic drugs, awakening drugs, sedative drugs, tranquilizers, cholinergic agents, chemotherapeutic drugs, radio pharmaceuticals, drugs for osteogenic induction, heparin neutralizer agents with bladder stand still, procoagulants, hemostatic agents, xanthine derivatives, hormones, proteins of natural origin or proteins synthesized by genetic engineering, glycoproteins, lipoproteins, oligonucleotides, antibodies, antigens, vasopressin, vasopressin analogs, epinephrine, selectin, procoagulation toxicants, inhibitors against plasminogen activating factor, platelet activators, bone-forming factors, bone growth factors, synthetic peptides having hemostatic action, and other pharmaceutical or therapeutic components. The composition for hard tissue repair of the present invention can also be used in drug delivery systems or as regenerative medicine by containing the above other component(s).

The composition for hard tissue repair may further contain bone morphogenetic factors, bone growth factors, and other pharmaceutical or therapeutic components for the purpose of promoting tissue repair.

Examples of the other components further include perfumes, etc., such as orange oil, grapefruit oil, lemon oil, lime oil, clove oil, wintergreen oil, peppermint oil, peppermint spirits, banana distillate, cucumber distillate, honey distillate, rose water, menthol, anethole, alkyl salicylate, benzaldehyde, monosodium glutamate, ethyl vanillin, thymol and vanillin, etc.

Examples of the other components may further include inorganic fillers (except for the above-mentioned X-ray contrast medium), organic fillers, organic composite fillers and colorants for the purpose of clarification of visual distinction from surrounding bone tissue, improvement of adhesion, enhancement of physical properties such as compressive strength, etc., or reducing harm to surrounding bone tissue by complementing active radical species.

Examples of the inorganic fillers include metal oxide powder such as bismuth oxide, titanium oxide, zinc oxide, aluminum oxide particles, etc.; metal salt powders such as zirconium phosphate, etc.; glass fillers such as silica glass, aluminum-containing glass, barium-containing glass, strontium-containing glass, zirconium silicate glass, etc.; fillers with sustained silver release; fillers with sustained calcium release; and fillers with sustained fluorine release. From a viewpoint of forming a strong bond between the inorganic filler and the monomer (A) after curing, surface-treated inorganic fillers by a surface treatment such as silane treatment, polymer coating, etc., are preferably used. One of these inorganic fillers can be used alone, or two or more inorganic fillers can be used in combination.

Examples of the filler having a sustained-release property of calcium include calcium dihydrogen phosphate, calcium dihydrogen phosphate monohydrate, calcium hydrogen phosphate, calcium hydrogen phosphate dihydrate, tricalcium phosphate, octacalcium phosphate, hydroxyapatite, fluoroapatite, chlorine apatite, carbonic acid-containing hydroxyapatite, calcium gluconate, calcium glucuronate, calcium lactate, calcium acetate, calcium sorbate, calcium sulfate dihydrate, calcium sulfate hemihydrate, tricalcium α-phosphate and tricalcium β-phosphate. One of these having a sustained-release property of calcium can be used alone or two or more fillers can be used in combination.

When the above-described daptomycin or a pharmacologically acceptable salt thereof is used as the antimicrobial drug particles (Y) and when it is used together with the filler having the sustained-release property of calcium, there is a tendency of improvement of its antimicrobial activity. In addition, when the above filler is used together with the above-mentioned antimicrobial agent particles (Y) and/or the above-mentioned polysaccharide (Z), there is a tendency that the antimicrobial activity is improved, and/or that harm to the living body is reduced.

Examples of the colorants (each color number is represented as Index by Japanese Color Name), include, Red No. 2 and aluminum lakes thereof, Red No. 3 and aluminum lakes thereof, Red No. 102 and aluminum lakes thereof, Red No. 104-(1) and aluminum lakes or barium lakes thereof, Reds No. 105-(1) and aluminum lakes thereof, Red No. 106 and aluminum lakes thereof, Yellow No. 4 and aluminum lakes, barium lakes or zirconium lakes thereof, Yellow No. 5 and aluminum lakes, barium lakes or zirconium lakes thereof, Green No. 3 and aluminum lakes thereof, Blue No. 1 and aluminum lakes, barium lakes or zirconium lakes thereof, Blue No. 2 and aluminum lakes thereof, Red No. 201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227 and aluminum lakes thereof, Red No. 228, Red No. 230-(1) and aluminum lakes thereof, Red No. 230-(2) and aluminum lakes thereof, Red No. 231 and aluminum lakes thereof, Red No. 232 and aluminum lakes thereof, Orange No. 201, Orange No. 203, Orange No. 204, Orange No. 205 and aluminum lakes, barium lakes or zirconium lakes thereof, Orange No. 206, Orange No. 207 and aluminum lakes thereof, Yellow No. 201, Yellow No. 202-(1) and aluminum lakes thereof, Yellow No. 202-(2) and aluminum lakes thereof, Yellow No. 203 and aluminum lakes, barium lakes or zirconium lakes thereof, Yellow No. 204, Yellow No. 205, Green No. 201 and aluminum lakes thereof, Green No. 202, Green No. 204 and aluminum lakes thereof, Green No. 205 and aluminum lakes or zirconium lakes thereof, Blue No. 201, Blue No. 202 and barium lakes thereof, Blue No. 203, Blue No. 204, Blue No. 205 and aluminum lakes thereof, Brown No. 201 and aluminum lakes thereof, Purple No. 201, Red No. 401 and aluminum lakes thereof, Red No. 404, Red No. 405, Red No. 501, Red No. 502 and aluminum lakes thereof, Red No. 503 and aluminum lakes thereof, Red No. 504 and aluminum lakes thereof, Red No. 505, Red No. 506 and aluminum lakes thereof, Orange No. 401, Orange No. 402 and aluminum lakes or barium lakes thereof, Orange No. 403, Yellow No. 401, Yellow No. 402 and aluminum lakes thereof, Yellow No. 403-(1) and aluminum lakes thereof, Yellow No. 404, Yellow No. 405, Yellow No. 406 and aluminum lakes thereof, Yellow No. 407 and aluminum lakes thereof, Green No. 401, Green No. 402 and aluminum lakes or barium lakes thereof, Blue No. 403, Blue No. 404, Purple No. 401 and aluminum lakes thereof, Black No. 401 and aluminum lakes thereof; chlorophyll, chlorophyllin, malachite green, crystal violet, brilliant green, cobalt phthalocyanine, carotene, vitamin B12 and derivatives derived therefrom.

One of these colorants can be used alone, or two or more colorants can be used in combination.

The addition amount of the colorant may be appropriately selected depending on the type thereof, and it is usually 0 to 5% by mass, preferably 0 to 2% by mass, and more preferably 0 to 1% by mass with respect to 100% by mass of the sum of the whole composition for hard tissue repair, that is, with respect to 100% by mass of the sum of the monomer (A), the polymer powder (B), the polymerization initiator (C) and the contrast medium (X) and/or the antimicrobial drug particles (Y) and other components to be contained if necessary.

[Composition for Hard Tissue Repair]

The composition for hard tissue repair according to the present invention is prepared by mixing the monomer (A), the polymer powder (B), the polymerization initiator (C) and the other components contained as needed. This composition can be used by applying to an affected area. In the present invention, the "composition for hard tissue repair" is used for mutual adhesion of hard tissues, filling into hard tissues, adhesion between hard tissues and artifacts such as titanium, ceramics, stainless steel, etc., and adhesion between hard tissues and other tissues such as soft tissues, etc., but does not include adhesion between teeth and filling materials (i.e., for dental use).

Upon mixing of these components, the order of mixing is not limited, and from the viewpoint that the stability of the composition for hard tissue repair to be obtained is more excellent, it is preferable that, first, the monomer (A) and the polymerization initiator (C) are mixed, and subsequently, the polymer powder (B) blended with both of the contrast medium (X) and the antimicrobial drug particles (Y) is mixed thereto. It is more preferable that the monomer (A), the polymerization initiator (C), and the polymer powder (B) blended with both of the contrast medium (X) and the antimicrobial drug particles (Y), are mixed simultaneously.

When the composition for hard tissue repair of the present invention contains a polymerization inhibitor, it is preferable that, first, a mixture of the monomer (A) and a polymerization inhibitor is mixed with the polymerization initiator (C), and, subsequently, the polymer powder (B) blended with both of the contrast medium (X) and the antimicrobial drug particles (Y) is mixed thereto, from the view point that the stability of the composition to be obtained is more excellent. It is more preferable that a mixture of the monomer (A) and a polymerization inhibitor; the polymerization initiator (C); and the polymer powder (B) blended with both of the contrast medium (X) and the antimicrobial drug particles (Y), are mixed simultaneously.

Prior to curing the composition for hard tissue repair of the present invention, the composition may be sterilized by treatments with dry-heat, steam, ethylene oxide (EO), a gas such as hydrogen peroxide, etc., or by filtration or treatment with a liquid, etc. Prior to filling of the composition for hard tissue repair of the present invention, the affected area may be disinfected beforehand with a disinfectant such as alcohol, etc. Before the affected area is filled with the composition for hard tissue repair, for example, a pre-treatment may be carried out for the purpose of improving adhesion to the affected area. As the liquid for the pre-treatment, for example, physiological saline is mentioned.

[Kit for Hard Tissue Repair]

When there is a case that the composition for hard tissue repair of the present invention may change in its form and performance over a long period of time and that the effects of the present invention may be impaired, it is possible that all of the components used for hard tissue repair comprising the monomer (A), the polymer powder (B), the polymerization initiator (C) and components to be contained as needed are separated each other as a single component; or divided in an optional combination and contained in three or more members and, then, stored as a kit for hard tissue repair. The stored components are mixed before use to prepare a composition for hard tissue repair. Examples of the members for storage include a gas-barrier sealable resin container and a glass ampoule in order to prevent volatilization and scattering of the monomer (A) and the polymerization initiator (C). The members for storage of the polymer powder (B) include resin and glass containers having a good sealability to prevent moisture absorption, or non-woven resin fabrics and sterilized papers for sterilization using a gas such as ethylene oxide (EO), hydrogen peroxide, etc.

As a method of storing the above components, for example, a preferable method comprises dividing all of the components into three portions, i. e., a mixture of the monomer (A) and the other components to be contained as needed; a mixture of the polymer powder (B) blended with both of the contrast medium (X) and the antimicrobial drug particles (Y) and the other components to be contained as needed; and a mixture of the polymerization initiator (C) and the other components to be contained as needed and, then, storing the mixtures thus divided. The other possible methods include, for example, a method comprising dividing the components into five portions, i. e., a mixture of the monomer (A) and the other components to be contained as needed; a mixture of the polymer powder (B) and the other components to be contained as needed; the contrast medium (X) and the other components to be contained as needed; the antimicrobial drug particles (Y) and the other components to be contained as needed; and the polymerization initiator (C) and the other components to be contained as needed, and storing the mixtures thus divided, as well as, a method comprising dividing the components into three portions, i. e., a mixture of the monomer (A), the contrast medium (X), the antimicrobial drug particles (Y) and other components to be contained as needed; a mixture of the polymer powder (B) and the other components to be contained as needed; and a mixture of the polymerization initiator (C) and other components to be contained as needed, and storing the mixtures thus divided.

These divided portions can be provided as the commercial products by filling them in the members separated each other, for example, containers, etc., such as ampoules, etc., and putting them in a kit for hard tissue repair.

The kit for hard tissue repair is not particularly limited in its parts structure, as long as the form and performance thereof are not changed by storage and the effect of the present invention is not impaired. Regarding a kit having preferable parts structure, the monomer (A); a mixture of the polymer powder (B) blended with both of the contrast medium (X) and the antimicrobial drug particles (Y) with other components to be contained as needed; and the polymerization initiator (C), are separately filled in the containers, wherein the monomer (A) and the polymerization initiator (C) are first mixed, and, subsequently, a mixture of the polymer powder (B) blended with both of the contrast medium (X) and the antimicrobial drug particles (Y) with other components to be contained as needed is mixed therewith. It is more preferable that the monomer (A); a mixture of the polymer powder (B) blended with both of the contrast medium (X) and the antimicrobial drug particles (Y) with other components to be contained as needed; and the polymerization initiator (C), are mixed simultaneously. According to such parts structure, a composition for hard tissue repair is easily obtained which has more stable performance.

The kit for hard tissue repair includes, for example, a kit comprising members (for example, resin container, glass ampoule) separately containing the monomer (A); the polymer powder (B) blended with both of the contrast medium (X) and the antimicrobial drug particles (Y); and the polymerization initiator (C), each other, as well as, a member for mixing the components taken out from the members (for example, orthopedic cement mixer, orthopedic cement injector, orthopedic cement dispenser, cement gun, container for mixing, dish for mixing, cylinder).

The kit for hard tissue repair includes, for example, a kit comprises three or more chambers separated each other by a partition or a spacer in a mixing container, in which the monomer (A), the polymer powder (B) blended with both of the contrast medium (X) and the antimicrobial drug particles (Y); and the polymerization initiator (C) are contained, respectively; and a mixing unit with a stirring blade set in advance enabling mixing by operating the stirring blade. According to the above kit, the monomer (A) and the polymerization initiator (C) pass through a bypass designed beforehand in the mixing container by destroying or moving the partition, or removing the spacer and contact the polymer powder (B) blended with both of the contrast medium (X) and the antimicrobial drug particles (Y), followed by mixing them in the mixing unit.

The kit consisting of one mixing container as above, in which the components are separately contained in three or more divided chambers can reduce complexity in comparison with a method in which the composition of the present invention is divided into two or more members, typically divided into the separate vessels, respectively and used by mixing them directly before use. Furthermore, since the kit consisting of one mixing container as above can fill the composition directly to an affected site by a jig such as a cement gun, etc., enabling to pour the composition directly from the mixing container, such kit is technically and economically useful.

In addition, a part or the whole component of the polymerization initiator (C) may be hold beforehand by a jig, which is used for coating the composition for hard tissue repair on the affected part of hard tissue, etc., such as bones and cartilages, etc.; soft tissue; and the other artificial products such as titanium, ceramics or stainless steel, etc. In this case, a composition for hard tissue repair according to the present invention can be prepared in situ, by bringing the jig into contact with either the monomer (A) or a mixture containing the monomer (A) and a polymerization inhibitor; the polymer powder (B) and the other components to be contained as needed, just before their use, and, then, the composition thus obtained can be filled in the affected part, as it is.

The jigs for filling the affected site with the composition include, for example, an orthopedic cement mixer, an orthopedic cement injector, an orthopedic cement dispenser, and cement gun.

The kit for hard tissue repair may have, for example, an antiseptic solution such as an alcohol, etc., described above or a solution for pretreatment for the purpose of improving adhesion, etc.

When components are packed for the kit for hard tissue repair, the components may be sterilized with an electromagnetic wave such as visible light, etc., preferably under the conditions wherein the components do not deteriorate (for example, the monomer does not cure).

EXAMPLES

Hereinafter, the present invention will be more specifically described based on the examples, but the present invention is not limited to these examples.

(1) Aspect Ratio Value (Ap Value) and Cumulative Ratio (%)

The Ap value and the cumulative ratio (%) were measured by using, as a dispersion solvent, 2-propanol (manufactured by Daishin Chemical Co., Ltd.), dispersing the sample for 60 seconds in an ultrasonic bath with an output of 500 W, and measuring the Ap value and the cumulative ratio (%) of the sample according to a dynamic image analysis method (wet method) using PITA-3 (manufactured by Seishin Enterprise Co., Ltd., particle size/shape distribution measuring instrument) under conditions of a sample liquid flow rate of 0.42 µL/sec, a carrier liquid flow rate of 416.67 µL/sec and an observation magnification (lens magnification) of 10 times. The number of observed particles was about 10,000 per one measurement. The Ap value was calculated by the following formula based on the projection image obtained by this dynamic image analysis method (wet method).

$Ap \text{ value} = L/W$

L: major axis (maximum length) (µm)

W: short axis (length in the direction vertical to the maximum length) (µm)

The cumulative ratio of the powder particles having Ap values of 1.00 or more and less than 1.10 was determined by graphing the distribution of the Ap values of the powder particle obtained by the measurement, as the cumulative distribution (the whole Ap value distribution of powder particles corresponds to 100 cumulative %), and calculating the proportion of distribution in which the Ap values corresponds to the range of 1.00 or more and less than 1.10.

(2) Volume Mean Particle Diameter D50

The volume mean particle diameter D50 of each polymer powder was measured by using, as a dispersing solvent, a special grade reagent methanol (solvent refractive index 1.33) (manufactured by Wako Pure Chemical Industries, Ltd.) or a 0.2% by mass aqueous solution of sodium hexametaphosphate (solvent refractive index 1.33) (manufactured by Wako Pure Chemical Industries, Ltd.), dispersing the sample by an ultrasonic homogenizer built in the device for 5 minutes (output 25 W), and measuring the volume mean particle diameter D50 of the sample using Microtrac MT3300EXII (manufactured by Microtrac, particle size distribution meter) at a circulation speed of 50% (at 100%, 65 mL/sec.) under the concentration condition in the appropriate amount range of the device Loading Index.

The value of the volume mean particle diameter D50 of each polymer powder (B) used in Examples and Comparative Examples is the value of the cumulative 50% as the volume mean particle diameter in the whole polymer powder (B), and the value of the volume mean particle diameter D50 of the polymer powder (B-x) is the value of the cumulative 50% as the volume mean particle diameter in the whole polymer powder (B-x), as well as the value of the volume mean particle diameter D50 of the polymer powder (B-y) is the value of the cumulative 50% as the volume mean particle diameter in the whole polymer powder (B-y).

(3) Amount of Eluted Monomer (mg/g)

The amount of eluted monomers (mg/g) was measured under the conditions prescribed in American Standard ASTM F451-16 (Standard Specification for Acrylic Bone Cement) regarding bone cement. For the elution operation, each composition for hard tissue repair after preparation was quickly fractioned in a rage of 0.8 to 0.9 g, and the contact area with water (elution liquid) was controlled to be about 0.65 cm². The elution temperature was 37° C. The elution period was set to 7 days (168 hours)±15 minutes from the point of 3 minutes after the start of preparation of the composition for hard tissue repair.

(4) Simulated Bone Penetrability (mm)

The simulated bone penetrability was measured as a penetration depth (mm) by impregnating a bone model simulating cancellous bone composed of a polyurethane foam having open cell porous (manufactured by Human Body Corp, trade name: SAW1522-507, porosity: 95%) with physiological saline (manufactured by Wako Pure Chemical Industries, Ltd., trade name: 0.01 mol/L phosphate buffered physiological saline), placing a composition as a sample at 5 minutes after the composition became a soft mass and had no more stringiness on the upper surface of the polyurethane foam, applying a load to the composition at a pressure of 75 kPa for 30 seconds and measuring the penetration depth (mm).

(5) Adhesion to Metal (kPa)

The adhesion to a metal material was measured as a resistance value by placing a composition as a sample within 30 seconds after the composition became a soft mass and had no more stringiness on the upper surface of mirror-processed SUS304, applying a load to the composition at a pressure of 150 kPa for 30 minutes, allowing the composition to still stand for 24±3 hours without applying load, and measuring the resistance value needed for peeling the cured product from the interface with SUS304. The resistance value was a value measured when one end of the cured composition was pressed (like shearing) in a direction parallel to the adhesion interface with SUS304 at a test speed of 5 mm/min.

As the metal plate of SUS304, a mirror-finished SUS304 plate (product number 304 #400 polishing cut plate) manufactured by Hakudo was used, and the operation and/or evaluation environments included 23±2° C. and a relative humidity of 40% RH or more.

(6) Dough Time (Minute' Second")

The dough time was measured under the conditions prescribed in International Standard ISO 5833: 2002 (Surgical Implant-Acrylic Resin Cement) regarding bone cement.

(7) Residual Monomer Amount (%)

The amount (%) of the residual monomers was measured according to a measuring method prescribed in JIS T6501: 2012 "Acrylic resin for denture base (residual amount of methyl methacrylate monomer)". The extraction time of the monomer liquid was set to 3 hours±10 minutes.

(8) Resistance Value (N) at Discharge from Syringe

The resistance value at the discharge from a syringe was measured as the resistance value when the pusher of a Neofeed (registered trademark) syringe (manufactured by Top Co., standard 20 mL) filled with the composition for hard tissue repair was pressed at a test speed of 100 mm/min. The test was started 2 minutes and 30 seconds after the beginning of the preparation of the composition for hard tissue repair. The resistance value was an average value of two measured values when the displacement (movement distance) of the presser became about 5±3 mm and about 50±5 mm.

(9) Surface Dissipation Energy Limit Value ($G_{IC}$ Value) (KJ/m$^2$)

The limit value of the surface dissipation energy ($G_{IC}$ value) was measured by the SENB (Single-edge-notch-bending) method prescribed in American Standard ASTM D5045-24 regarding plastic materials. The plate thickness B of the SENB test piece was 4.0 mm, and the test speed was 10 mm/min.

Examples 1 to 6 and Comparative Examples 1 to 3

In Examples 1, 3, 4, 6 and Comparative Examples 1 and 3, methyl methacrylate was used as the monomer (A), a mixture of 85% by mass of partially oxidized tributylboron and 15% by mass of ethanol (manufactured by Mitsui Chemicals, Inc., product number: BC-S1i) was used as the polymerization initiator (C) (the sum of the polymerization initiator (C) is taken as 100% by mass), and barium sulfate (manufactured by Sakai Chemical Industry Co., Ltd.) was used, as the contrast medium (X).

In Example 2, 5 and Comparative Example 2, a mixture of 99.5% by mass of methyl methacrylate and 0.5% by mass of first class reagent N,N-dimethyl-p-toluidine (manufactured by Wako Pure Chemical Industries) was used as the monomer (A) (the sum of the monomer (A) is taken as 100% by mass), benzoyl peroxide (BPO) (manufactured by Aldrich Co., Ltd., trade name: Luperox® A75) was used as the polymerization initiator (C), and barium sulfate (manufactured by Sakai Chemical Industry Co., Ltd.) was used, as the contrast medium (X).

In Example 3 and Comparative Example 3, gentamicin sulfate (manufactured by Wako Pure Chemical Industries, Ltd., titer=654 μg/mg) was used as the antimicrobial drug particles (Y).

In Examples 1 to 6, polymethyl methacrylate (aspect ratio=1.30, weight average molecular weight Mw=452,000, volume mean particle diameter D50=18.7 μm) or polymethyl methacrylate (aspect ratio=1.72, weight average molecular weight Mw=457,000, volume mean particle diameter D50=21.7 μm) was used, as the polymer powder (B-x).

In Examples 1a to 1d, Example 1h, Examples 2a to 2b, Example 4a and Comparative Examples 1 to 3, (1) polymethyl methacrylate (aspect ratio=1.04, weight average molecular weight Mw=117,000, volume mean particle diameter D50=8.2 μm) and (2) polymethyl methacrylate (aspect ratio=1.04, weight average molecular weight Mw=147,000, volume mean particle diameter D50=40.5 μm) were used in combination (weight ratio (1):(2)=38.9: 61.1), as the polymer powder (B-y).

In Examples 1e to 1g, Examples 1i to 1 k, Examples 2c to 2e, Example 3, Examples 4b to 4c and Example 5, polymethyl methacrylate (aspect ratio=1.03, weight average molecular weight Mw=139,000, volume mean particle diameter D50=70.5 μm) was used, as the polymer powder (B-y).

In Example 6, (1) polymethyl methacrylate (aspect ratio=1.04, weight average molecular weight Mw=117,000, volume mean particle diameter D50=8.2 μm) and (2) polymethyl methacrylate (aspect ratio=1.04, weight average molecular weight Mw=147,000, volume mean particle diameter D50=40.5 μm) were used in combination (mass ratio (1):(2)=22.2: 77.8), as the polymer powder (B-y).

Then, mixtures obtained previously by uniformly dispersing the polymer powder (B) and the contrast medium (X), and if necessary, the antimicrobial drug particles (Y) at blending ratios shown in Tables 1 to 3, Tables 11 to 12, Tables 18 and 19, Table 22, Table 25 and Table 28 were mixed with the monomer (A) and the polymerization initiator (C) previously mixed in 50 mL glass sample tubes at blending ratios shown in Tables 1 to 3, Tables 11 to 12, Tables 18 to 19, Table 22, Table 25 and Table 28, respectively, by using a polypropylene container (manufactured by Shofusha, trade name: tray resin mixer) and a spatula made of silicone rubber, and the properties were measured by the methods explained above. The mixing time was 60 seconds. The results are shown in Tables 4 to 10, Tables 13 to 17, Tables 20 to 21, Tables 23 to 24, Tables 26 to 27 and Tables 29 to 30, respectively.

The blending ratio shown in the parentheses for each component in the tables is a ratio (parts by mass) based on 100 parts by mass of the sum of the components (A) to (C). Further, the blending ratio of the components (B-x) and (B-y) is a ratio (% by mass) based on 100% by mass of the polymer powder (B).

The Ap value of the polymer powder (B) in the tables is the value of cumulative 50% of the aspect ratio in the whole polymer powder (B), and the Ap value of the polymer powder (B-x) is the value of cumulative 50% of the aspect ratio in the whole polymer powder (B-x), as well as, the Ap value of the polymer powder (B-y) is the value of cumulative 50% of the aspect ratio in the whole polymer powder (B-y).

In the column of "Cumulative ratio (%) of powder particles having Ap values of less than 1.10" in the tables, the cumulative ratio (%) of the polymer powder (B) is the value of the cumulative ratio (%) of powder particles having Ap values of less than 1.10 in the whole polymer powder (B); and the cumulative ratio (%) of the whole powder particle is the value of the cumulative ratio (%) of powder particles having Ap values of less than 1.10 in the whole mixture of the polymer powder (B) and the contrast medium (X) (i.e., all of the particles contained in the composition).

TABLE 1

(Polymerization initiator (C): Organic boron compound type)

| | Composition for hard tissue repair (Parts by mass) | | Ap value | Cumulative ratio (%) of powder particles having Ap values of less than 1.10 | |
|---|---|---|---|---|---|
| | | | | Polymer powder(B) | Whole powder particles |
| Example 1a | Monomer (A) | 18.8 g(33.2) | — | 67.1 | 58.0 |
| | Polymer powder (B) | 36.0 g(63.6) | 1.14 | | |
| | (B-x) | 5.6% | 1.30 | | |
| | (B-y) | 94.4% | 1.04 | | |
| | Polymerization initiator (C) | 1.8 g(3.2) | — | | |
| | Contrast medium (X) | 4.0 g(7.1) | — | | |
| Example 1b | Monomer (A) | 18.8 g(33.2) | — | 42.7 | 26.7 |
| | Polymer powder (B) | 36.0 g(63.6) | 1.16 | | |
| | (B-x) | 11.1% | 1.30 | | |
| | (B-y) | 88.9% | 1.04 | | |
| | Polymerization initiator (C) | 1.8 g(3.2) | — | | |
| | Contrast medium (X) | 4.0 g(7.1) | — | | |
| Example 1c | Monomer (A) | 18.8 g(33.2) | — | 44.9 | 27.3 |
| | Polymer powder (B) | 36.0 g(63.6) | 1.19 | | |
| | (B-x) | 16.7% | 1.30 | | |
| | (B-y) | 83.3% | 1.04 | | |
| | Polymerization initiator (C) | 1.8 g(3.2) | — | | |
| | Contrast medium (X) | 4.0 g(7.1) | — | | |
| Example 1d | Monomer (A) | 18.8 g(33.2) | — | 44.4 | 27.2 |
| | Polymer powder (B) | 36.0 g(63.6) | 1.21 | | |
| | (B-x) | 17.2% | 1.30 | | |
| | (B-y) | 82.8% | 1.04 | | |
| | Polymerization initiator (C) | 1.8 g(3.2) | — | | |
| | Contrast medium (X) | 4.0 g(7.1) | — | | |
| Example 1e | Monomer(A) | 18.8 g(33.2) | — | 38.8 | 21.7 |
| | Polymer powder (B) | 36.0 g(63.6) | 1.19 | | |
| | (B-x) | 18.4% | 1.30 | | |
| | (B-y) | 81.6% | 1.03 | | |
| | Polymerization initiator (C) | 1.8 g(3.2) | — | | |
| | Contrast medium (X) | 4.0 g(7.1) | — | | |
| Example 1f | Monomer (A) | 18.8 g(33.2) | — | 40.7 | 24.0 |
| | Polymer powder (B) | 36.0 g(63.6) | 1.21 | | |
| | (B-x) | 22.2% | 1.30 | | |
| | (B-y) | 77.8% | 1.03 | | |
| | Polymerization initiator (C) | 1.8 g(3.2) | — | | |
| | Contrast medium (X) | 4.0 g(7.1) | — | | |

TABLE 2

(Polymerization initiator (C): Organic boron compound type)

|  | Composition for hard tissue repair (Parts by mass) | | Ap value | Cumulative ratio (%) of powder particles having Ap values of less than 1.10 | |
|---|---|---|---|---|---|
|  |  |  |  | Polymer powder(B) | Whole powder particles |
| Example 1g | Monomer (A) | 18.8 g(33.2) | — | 28.9 | 15.5 |
|  | Polymer powder (B) | 36.0 g(63.6) | 1.29 |  |  |
|  | (B-x) | 26.7% | 1.30 |  |  |
|  | (B-y) | 73.3% | 1.03 |  |  |
|  | Polymerization initiator (C) | 1.8 g(3.2) | — |  |  |
|  | Contrast medium (X) | 4.0 g(7.1) | — |  |  |
| Example 1h | Monomer (A) | 18.8 g(33.2) | — | 26.0 | 12.7 |
|  | Polymer powder (B) | 36.0 g(63.6) | 1.32 |  |  |
|  | (B-x) | 27.8% | 1.30 |  |  |
|  | (B-y) | 72.2% | 1.04 |  |  |
|  | Polymerization initiator (C) | 1.8 g(3.2) | — |  |  |
|  | Contrast medium (X) | 4.0 g(7.1) | — |  |  |
| Example 1i | Monomer(A) | 18.8 g(33.2) | — | 24.4 | 9.7 |
|  | Polymer powder (B) | 36.0 g(63.6) | 1.33 |  |  |
|  | (B-x) | 33.3% | 1.30 |  |  |
|  | (B-y) | 66.7% | 1.03 |  |  |
|  | Polymerization initiator (C) | 1.8 g(3.2) | — |  |  |
|  | Contrast medium (X) | 4.0 g(7.1) | — |  |  |
| Example 1j | Monomer (A) | 18.8 g(33.2) | — | 18.7 | 3.5 |
|  | Polymer powder (B) | 36.0 g(63.6) | 1.34 |  |  |
|  | (B-x) | 38.9% | 1.30 |  |  |
|  | (B-y) | 61.1% | 1.03 |  |  |
|  | Polymerization initiator (C) | 1.8 g(3.2) | — |  |  |
|  | Contrast medium (X) | 4.0 g(7.1) | — |  |  |
| Example 1k | Monomer (A) | 18.8 g(33.2) | — | 17.4 | 3.3 |
|  | Polymer powder (B) | 36.0 g(63.6) | 1.35 |  |  |
|  | (B-x) | 50.0% | 1.30 |  |  |
|  | (B-y) | 50.0% | 1.03 |  |  |
|  | Polymerization initiator (C) | 1.8 g(3.2) | — |  |  |
|  | Contrast medium(X) | 4.0 g(7.1) | — |  |  |

TABLE 3

(Polymerization initiator (C): Organic boron compound type)

|  | Composition for hard tissue repair (Parts by mass) | | Ap value | Cumulative ratio (%) of powder particles having Ap values of less than 1.10 | |
|---|---|---|---|---|---|
|  |  |  |  | Polymer powder(B) | Whole powder particles |
| Comparative example 1a | Monomer (A) | 18.8 g(33.2) | — | 86.3 | 69.3 |
|  | Polymer powder (B) | 36.0 g(63.6) | 1.04 |  |  |
|  | (B-x) | 0.0% | — |  |  |
|  | (B-y) | 100.0% | 1.04 |  |  |
|  | Polymerization initiator (C) | 1.8 g(3.2) | — |  |  |
|  | Contrast medium(X) | 4.0 g(7.1) | — |  |  |
| Comparative example 1b | Monomer (A) | 22.6 g(37.2) | — | 86.3 | 69.3 |
|  | Polymer powder (B) | 36.0 g(59.2) | 1.04 |  |  |
|  | (B-x) | 0.0% | — |  |  |
|  | (B-y) | 100.0% | 1.04 |  |  |
|  | Polymerization initiator (C) | 2.2 g(3.6) | — |  |  |
|  | Contrast medium (X) | 4.0 g(6.6) | — |  |  |
| Comparative example 1c | Monomer (A) | 15.0 g(28.6) | — | 86.3 | 69.3 |
|  | Polymer powder (B) | 36.0 g(68.7) | 1.04 |  |  |
|  | (B-x) | 0.0% | — |  |  |
|  | (B-y) | 100.0% | 1.04 |  |  |
|  | Polymerization initiator (C) | 1.4 g(2.7) | — |  |  |
|  | Contrast medium(X) | 4.0 g(7.6) | — |  |  |

TABLE 4

(Polymerization initiator (C): Organic boron compound type)

| | Eluted monomer amount (mg/g) |
|---|---|
| Example 1a | 1.46 |
| Example 1b | 1.51 |
| Example 1c | 1.49 |
| Example 1d | 1.29 |
| Example 1f | 1.11 |
| Example 1h | 0.88 |
| Example 1i | 0.79 |
| Example 1j | 0.75 |
| Example 1k | 0.71 |
| Comparative example 1b | 3.46 |

TABLE 5

(Polymerization initiator (C): Organic boron compound type)

| | Simulated bone penetrability (mm) |
|---|---|
| Example 1a | 1.31 |
| Example 1b | 1.36 |
| Example 1c | 1.41 |
| Example 1d | 1.81 |
| Example 1e | 5.66 |
| Example 1f | 5.22 |
| Example 1g | 1.88 |
| Example 1i | 1.29 |
| Example 1j | 1.04 |
| Comparative example 1a | 0.12 |

TABLE 6

(Polymerization initiator (C): Organic boron compound type)

| | Adhesion to metal (kPa) |
|---|---|
| Example 1a | 127 |
| Example 1b | 150 |
| Example 1d | 135 |
| Example 1f | 109 |
| Example 1i | 96 |
| Example 1j | 71 |
| Comparative example 1a | 31 |

TABLE 7

(Polymerization initiator (C): Organic boron compound type)

| | Dough time (minute' second") |
|---|---|
| Example 1a | 4'55" |
| Example 1b | 4'10" |
| Example 1d | 3'35" |
| Example 1f | 3'15" |

TABLE 7-continued (Polymerization initiator (C): Organic boron compound type)

| | Dough time (minute' second") |
|---|---|
| Example 1h | 3'00" |
| Example 1i | 2'45" |
| Example 1j | 2'20" |
| Example 1k | 1'15" |
| Comparative example 1a | 6'30" |
| Comparative example 1b | 7'15" |

TABLE 8

(Polymerization initiator (C): Organic boron compound type)

| | Residual monomer amount (%) |
|---|---|
| Example 1b | 4.05 |
| Example 1c | 3.65 |
| Example 1d | 3.26 |
| Example 1f | 2.90 |
| Example 1h | 2.81 |
| Example 1i | 2.79 |
| Example 1j | 2.22 |
| Comparative example 1a | 5.44 |
| Comparative example 1b | 5.77 |

TABLE 9

(Polymerization initiator (C): Organic boron compound type)

| | Resistance value (N) at discharge from syringe |
|---|---|
| Example 1a | 49.2 |
| Example 1b | 34.4 |
| Example 1d | 42.3 |
| Example 1f | 55.5 |
| Example 1h | 61.0 |
| Example 1i | 61.8 |
| Example 1j | 76.2 |
| Comparative example 1a | 86.0 |
| Comparative example 1c | 110.2 |

TABLE 10

(Polymerization initiator (C): Organic boron compound type)

| | $G_{IC}$ value (kJ/m$^2$) |
|---|---|
| Example 1a | 0.70 |
| Example 1b | 0.86 |
| Example 1d | 0.93 |
| Example 1f | 0.97 |
| Example 1j | 1.02 |
| Comparative example 1a | 0.59 |

TABLE 11

(Polymerization initiator (C): BPO type)

| | Composition for hard tissue repair (Parts by mass) | | Ap value | Polymer powder(B) | Whole powder particles |
|---|---|---|---|---|---|
| | | | | Cumulative ratio (%) of powder particles having Ap values of less than 1.10 | |
| Example 2a | Monomer (A) | 18.7 g(34.1) | — | 67.1 | 58.0 |
| | Polymer powder (B) | 36.0 g(65.7) | 1.14 | | |

TABLE 11-continued (Polymerization initiator (C): BPO type)

|  | Composition for hard tissue repair (Parts by mass) | | Ap value | Cumulative ratio (%) of powder particles having Ap values of less than 1.10 | |
|---|---|---|---|---|---|
|  |  |  |  | Polymer powder(B) | Whole powder particles |
| Example 2b | (B-x) | 5.6% | 1.30 |  |  |
|  | (B-y) | 94.4% | 1.04 |  |  |
|  | Polymerization initiator (C) | 0.10 g(0.2) | — |  |  |
|  | Contrast medium (X) | 4.0 g(7.1) | — |  |  |
|  | Monomer (A) | 18.7 g(34.1) | — | 44.4 | 27.2 |
|  | Polymer powder (B) | 36.0 g(65.7) | 1.21 |  |  |
|  | (B-x) | 17.2% | 1.30 |  |  |
|  | (B-y) | 82.8% | 1.04 |  |  |
|  | Polymerization initiator (C) | 0.10 g(0.2) | — |  |  |
|  | Contrast medium (X) | 4.0 g(7.1) | — |  |  |
| Example 2c | Monomer(A) | 18.7 g(34.1) | — | 32.9 | 19.8 |
|  | Polymer powder (B) | 36.0 g(65.7) | 1.21 |  |  |
|  | (B-x) | 22.2% | 1.30 |  |  |
|  | (B-y) | 77.8% | 1.03 |  |  |
|  | Polymerization initiator (C) | 0.10 g(0.2) | — |  |  |
|  | Contrast medium (X) | 4.0 g(7.1) | — |  |  |
| Example 2d | Monomer(A) | 18.7 g(34.1) | — | 18.7 | 3.5 |
|  | Polymer powder (B) | 36.0 g(65.7) | 1.34 |  |  |
|  | (B-x) | 38.9% | 1.30 |  |  |
|  | (B-y) | 61.1% | 1.03 |  |  |
|  | Polymerization initiator (C) | 0.10 g(0.2) | — |  |  |
|  | Contrast medium (X) | 4.0 g(7.1) | — |  |  |
| Example 2e | Monomer (A) | 18.7 g(34.1) | — | 17.4 | 3.3 |
|  | Polymer powder (B) | 36.0 g(65.7) | 1.35 |  |  |
|  | (B-x) | 50.0% | 1.30 |  |  |
|  | (B-y) | 50.0% | 1.03 |  |  |
|  | Polymerization initiator (C) | 0.10 g(0.2) | — |  |  |
|  | Contrast medium(X) | 4.0 g(7.1) | — |  |  |

TABLE 12

(Polymerization initiator (C): BPO type)

|  | Composition for hard tissue repair (Parts by mass) | | Ap value | Cumulative ratio (%) of powder particles having Ap values of less than 1.10 | |
|---|---|---|---|---|---|
|  |  |  |  | Polymer powder(B) | Whole powder particles |
| Comparative example 2 | Monomer (A) | 18.7 g(34.1) | — | 89.0 | 76.6 |
|  | Polymer powder (B) | 36.0 g(65.7) | 1.04 |  |  |
|  | (B-x) | 0.0% | — |  |  |
|  | (B-y) | 100.0% | 1.04 |  |  |
|  | Polymerization initiator (C) | 0.10 g(0.2) | — |  |  |
|  | Contrast medium (X) | 4.0 g(7.1) | — |  |  |

TABLE 13

(Polymerization initiator (C): BPO type)

|  | Eluted monomer amount (mg/g) |
|---|---|
| Example 2a | 1.79 |
| Example 2b | 1.94 |
| Example 2c | 1.76 |
| Example 2d | 1.65 |
| Example 2e | 1.14 |
| Comparative example 2 | 3.10 |

TABLE 14

(Polymerization initiator (C): BPO type)

|  | Simulated bone penetrability (mm) | Adhesion to metal (kPa) |
|---|---|---|
| Example 2a | 1.23 | 109 |
| Example 2b | 1.40 | 112 |
| Example 2c | 5.86 | 99 |
| Example 2d | 1.46 | 69 |
| Comparative example 2 | 0.49 | 20 |

TABLE 15

(Polymerization initiator (C): BPO type)

| | Dough time (minute' second") |
|---|---|
| Example 2a | 4'55" |
| Example 2b | 3'45" |
| Example 2c | 3'55" |
| Example 2d | 2'55" |
| Example 2e | 1'30" |
| Comparative example 2 | 6'50" |

TABLE 16

(Polymerization initiator (C): BPO type)

| | Residual monomer amount (%) | Resistance value (N) at discharge from syringe |
|---|---|---|
| Example 2a | 3.91 | 50.8 |
| Example 2b | 4.20 | 49.8 |
| Example 2c | 3.77 | 61.8 |
| Example 2d | 3.06 | 79.4 |
| Comparative example 2 | 5.89 | 104.6 |

TABLE 17

(Polymerization initiator (C): BPO type)

| | $G_{IC}$ value (kJ/m$^2$) |
|---|---|
| Example 2b | 0.61 |
| Example 2c | 0.69 |
| Example 2d | 0.73 |
| Comparative example 2 | 0.37 |

As shown in Tables 4 to 10 and Tables 13 to 17, the compositions for hard tissue repair of Examples 1 and 2 were excellent in various properties.

On the other hand, the compositions for hard tissue repair of Comparative Examples 1 and 2 were poor in some properties, because the polymer powder (B-x) having an aspect ratio of 1.10 or more was not contained and the cumulative ratio of powder particles having an aspect ratio of 1.00 or more and less than 1.10 in the whole powder particles was large.

In addition, Example 1, in which the organic boron compound (c1) was used as the polymerization initiator (C), was more excellent in some properties than Example 2, in which benzoyl peroxide (BPO) was used as the polymerization initiator (C). For example, when the set of Example 1a and Example 2a and the set of Example 1d and Example 2b, in each of which the formulations other than the polymerization initiator (C) are approximately the same, are directly compared, Examples 1a and 1d using the organic boron compound (c1) as the polymerization initiator (C) were more excellent in any one of the amount of eluted monomers (Tables 4 and 13), the simulated bone penetrability (Tables 5 and 14) and the adhesion to a metal (Tables 6 and 14).

TABLE 18

(Polymerization initiator (C): Organic boron compound type)

| | Composition for hard tissue repair (Parts by mass) | | Ap value | Cumulative ratio (%) of powder particles having Ap values of less than 1.10 Polymer powder(B) | Whole powder particles |
|---|---|---|---|---|---|
| Example 3a | Monomer (A) | 18.8 g(33.2) | — | 40.7 | 23.5 |
| | Polymer powder (B) | 36.0 g(63.6) | 1.21 | | |
| | (B-x) | 22.2% | 1.30 | | |
| | (B-y) | 77.8% | 1.03 | | |
| | Polymerization initiator (C) | 1.8 g(3.2) | — | | |
| | Contrast medium (X) | 4.0 g(7.1) | — | | |
| | Antimicrobial drug particles (Y) | 1.0 g(1.8) | — | | |
| Example 3b | Monomer(A) | 18.8 g(33.2) | — | 40.7 | 16.5 |
| | Polymer powder (B) | 36.0 g(63.6) | 1.21 | | |
| | (B-x) | 22.2% | 1.30 | | |
| | (B-y) | 77.8% | 1.03 | | |
| | Polymerization initiator (C) | 1.8 g(3.2) | — | | |
| | Contrast medium (X) | 4.0 g(7.1) | — | | |
| | Antimicrobial drug particles (Y) | 3.0 g(5.3) | — | | |
| Example 3c | Monomer (A) | 18.8 g(33.2) | — | 40.7 | 14.3 |
| | Polymer powder (B) | 36.0 g(63.6) | 1.21 | | |
| | (B-x) | 22.2% | 1.30 | | |
| | (B-y) | 77.8% | 1.03 | | |
| | Polymerization initiator (C) | 1.8 g(3.2) | — | | |
| | Contrast medium(X) | 4.0 g(7.1) | — | | |
| | Antimicrobial drug particles (Y) | 6.0 g(10.6) | — | | |

TABLE 19

(Polymerization initiator (C): Organic boron compound type)

| | Composition for hard tissue repair (Parts by mass) | | Ap value | Cumulative ratio (%) of powder particles having Ap values of less than 1.10 | |
|---|---|---|---|---|---|
| | | | | Polymer powder(B) | Whole powder particles |
| Comparative example 3a | Monomer (A) | 18.8 g(33.2) | — | 86.3 | 67.1 |
| | Polymer powder (B) | 36.0 g(63.6) | 1.04 | | |
| | (B-x) | 0.0% | — | | |
| | (B-y) | 100.0% | 1.04 | | |
| | Polymerization initiator (C) | 1.8 g(3.2) | — | | |
| | Contrast medium (X) | 4.0 g(7.1) | — | | |
| | Antimicrobial drug particles (Y) | 1.0 g(1.8) | — | | |
| Comparative example 3b | Monomer (A) | 22.6 g(37.2) | — | 86.3 | 67.1 |
| | Polymer powder (B) | 36.0 g(59.2) | 1.04 | | |
| | (B-x) | 0.0% | — | | |
| | (B-y) | 100.0% | 1.04 | | |
| | Polymerization initiator (C) | 2.2 g(3.6) | — | | |
| | Contrast medium (X) | 4.0 g(6.6) | — | | |
| | Antimicrobial drug particles (Y) | 1.0 g(1.6) | — | | |

TABLE 20

(Polymerization initiator (C): Organic boron compound type)

| | Eluted monomer amount (mg/g) | Residual monomer amount (%) |
|---|---|---|
| Example3a | 1.28 | 2.64 |
| Example3b | 1.27 | 2.62 |
| Example3c | 1.39 | 3.23 |
| Comparative example 3b | 3.60 | 5.60 |

TABLE 21

(Polymerization initiator (C): Organic boron compound type)

| | Simulated bone penetrability (mm) |
|---|---|
| Example 3a | 3.23 |
| Example 3b | 4.23 |

TABLE 21-continued (Polymerization initiator (C): Organic boron compound type)

| | Simulated bone penetrability (mm) |
|---|---|
| Example 3c | 4.78 |
| Comparative example 3a | 0.44 |

As shown in Tables 20 to 21, the composition for hard tissue repair of Example 3 was excellent in various properties.

On the other hand, the composition for hard tissue repair of Comparative Example 3 was poor in some properties, because the polymer powder (B-x) having an aspect ratio of 1.10 or more was not contained and the cumulative ratio of powder particles having an aspect ratio of 1.00 or more and less than 1.10 in the whole powder particle was large.

TABLE 22

(Polymerization initiator (C): Organic boron compound type)

| | Composition for hard tissue repair (Parts by mass) | | Ap value | Cumulative ratio (%) of powder particles having Ap values of less than 1.10 | |
|---|---|---|---|---|---|
| | | | | Polymer powder(B) | Whole powder particles |
| Example 4a | Monomer (A) | 18.8 g(33.2) | — | 44.0 | 30.2 |
| | Polymer powder (B) | 36.0 g(63.6) | 1.70 | | |
| | (B-x) | 11.1% | 1.72 | | |
| | (B-y) | 88.9% | 1.04 | | |
| | Polymerization initiator (C) | 1.8 g(3.2) | — | | |
| | Contrast medium (X) | 4.0 g(7.1) | — | | |
| Example 4b | Monomer (A) | 18.8 g(33.2) | — | 30.2 | 19.1 |
| | Polymer powder (B) | 36.0 g(63.6) | 1.69 | | |
| | (B-x) | 22.2% | 1.72 | | |
| | (B-y) | 77.8% | 1.03 | | |
| | Polymerization initiator (C) | 1.8 g(3.2) | — | | |
| | Contrast medium (X) | 4.0 g(7.1) | — | | |

TABLE 22-continued (Polymerization initiator (C): Organic boron compound type)

|   | Composition for hard tissue repair (Parts by mass) | | Ap value | Cumulative ratio (%) of powder particles having Ap values of less than 1.10 | |
|---|---|---|---|---|---|
|   |   |   |   | Polymer powder(B) | Whole powder particles |
| Example 4c | Monomer (A) | 18.8 g(33.2) | — | 25.7 | 7.7 |
|   | Polymer powder (B) | 36.0 g(63.6) | 1.73 | | |
|   | (B-x) | 33.3% | 1.72 | | |
|   | (B-y) | 66.7% | 1.03 | | |
|   | Polymerization initiator (C) | 1.8 g(3.2) | — | | |
|   | Contrast medium(X) | 4.0 g(7.1) | — | | |

TABLE 23

(Polymerization initiator (C): Organic boron compound type)

|   | Eluted monomer amount (mg/g) | Simulated bone penetrability (mm) |
|---|---|---|
| Example 4a | 1.33 | 1.94 |
| Example 4b | 0.91 | 5.07 |
| Example 4c | 0.74 | 2.22 |

TABLE 24

(Polymerization initiator (C): Organic boron compound type)

|   | Residual monomer amount (%) |
|---|---|
| Example 4a | 3.50 |
| Example 4b | 2.62 |
| Example 4c | 2.41 |

TABLE 25

(Polymerization initiator (C): BPO type)

|   | Composition for hard tissue repair (Parts by mass) | | Ap value | Cumulative ratio (%) of powder particles having Ap values of less than 1.10 | |
|---|---|---|---|---|---|
|   |   |   |   | Polymer powder(B) | Whole powder particles |
| Example 5a | Monomer (A) | 18.7 g(34.1) | — | 34.2 | 24.1 |
|   | Polymer powder (B) | 36.0 g(65.7) | 1.72 | | |
|   | (B-x) | 17.2% | 1.72 | | |
|   | (B-y) | 82.8% | 1.03 | | |
|   | Polymerization initiator (C) | 0.10 g(0.2) | — | | |
|   | Contrast medium (X) | 4.0 g(7.1) | — | | |
| Example 5b | Monomer(A) | 18.7 g(34.1) | — | 30.2 | 19.1 |
|   | Polymer powder (B) | 36.0 g(65.7) | 1.69 | | |
|   | (B-x) | 22.2% | 1.72 | | |
|   | (B-y) | 77.8% | 1.03 | | |
|   | Polymerization initiator (C) | 0.10 g(0.2) | — | | |
|   | Contrast medium(X) | 4.0 g(7.1) | — | | |

TABLE 26

(Polymerization initiator (C): BPO type)

|   | Eluted monomer amount (mg/g) | Simulated bone penetrability (mm) |
|---|---|---|
| Example 5a | 1.66 | 3.26 |
| Example 5b | 1.38 | 4.30 |

TABLE 27

| (Polymerization initiator (C): BPO type) | |
|---|---|
| | Residual monomer amount (%) |
| Example 5a | 4.01 |
| Example 5b | 3.48 |

As shown in Tables 23 to 24 and Tables 26 to 27, the compositions for hard tissue repair of Examples 4 to 5 were excellent in various properties.

In addition, Example 4, in which the organic boron compound (c1) was used as the polymerization initiator (C), was more excellent in some properties than Example 5, in which benzoyl peroxide (BPO) was used as the polymerization initiator (C). For example, when Example 4b and Example 5b, in which the formulations other than the polymerization initiator (C) are approximately the same, is compared, Example 4b using the organic boron compound (c1) as the polymerization initiator (C) was more excellent in any one of the amount of eluted monomers (Tables 23 and 26), the simulated bone penetrability (Tables 23 and 26), and the amount of the residual monomers (Tables 24 and 27).

TABLE 28

| (Polymerization initiator (C): Organic boron compound type) | | | | |
|---|---|---|---|---|
| | | | | Cumulative ratio (%) of powder particles having Ap values of less than 1.10 |
| Composition for hard tissue repair (Parts by mass) | | Ap value | Polymer powder(B) | Whole powder particles |
| Example 6 | Monomer (A) | 18.8 g(40.3) | — | 39.5 | 10.4 |
| | Polymer powder (B) | 26.0 g(55.8) | 1.22 | | |
| | (B-x) | 23.1% | 1.30 | | |
| | (B-y) | 76.9% | 1.04 | | |
| | Polymerization initiator (C) | 1.8 g(3.9) | — | | |
| | Contrast medium(X) | 14.0 g(30.0) | — | | |

TABLE 29

| (Polymerization initiator (C): Organic boron compound type) | | |
|---|---|---|
| | Eluted monomer amount (mg/g) | Simulated bone penetrability (mm) |
| Example 6 | 1.40 | 5.15 |

TABLE 30

| (Polymerization initiator (C): Organic boron compound type) | |
|---|---|
| | Residual monomer amount (%) |
| Example 6 | 3.09 |

As shown in Tables 29 to 30, the composition for hard tissue repair of Example 6 was excellent in various properties.

INDUSTRIAL AVAILABILITY

The composition for hard tissue repair according to the present invention is useful, for example, as a material for a bone cement, a filler for a bone defect, a bone filling material, an artificial bone, etc., wherein the bone cement is used for mutual adhesion between hard tissues, filling into hard tissues, adhesion and/or intimate contact between hard tissues and artifacts such as titanium, ceramics, stainless steel, etc., adhesion and/or intimate contact between hard tissues and other tissues such as soft tissues, etc., and fixing hard tissues such as bone, cartilage, etc., to an artificial joint, etc.

Further, when the composition for hard tissue repair of the present invention contains antimicrobial drug particles (Y), it is also useful as a material for molding of a medical cement spacer and a cement bead. For example, when the affected site becomes infected after the artificial joint surgery, there is a case that the inserted artificial joint is removed. A cement spacer containing an antibiotic is usually used to fill the gap created by this removal with the cement spacer. In some cases, only debridement (removal and cleaning of necrotic tissue) is performed without removing the artificial joint, and the cement beads containing the antimicrobial drug are embedded. Furthermore, there is a report using a bendable spacer. For example, a cement spacer or cement beads having a desired shape can be obtained, by curing the composition for hard tissue repair of the present invention in a mold for molding.

The invention claimed is:

1. A composition for hard tissue repair comprising a monomer (A), a polymer powder (B) and a polymerization initiator (C), wherein
   the polymer powder (B) comprises a polymer powder (B-x) having an aspect ratio of 1.10 or more, and
   the cumulative ratio of powder particles having aspect ratios of 1.00 or more and less than 1.10 in all of the powder particles contained in the composition for hard tissue repair is 2.5 cumulative % or more, and 65 cumulative % or less,
   the monomer (A) is a (meth) acrylate-based monomer,
   the polymer powder (B) is a polymethyl (meth) acrylate powder,
   the polymerization initiator (C) comprises an organic boron compound (c1), the blending amount of the monomer (A) is 10-45% of the total mass of the components (A) to (C),
   the blending amount of the polymer powder (B) is 54.9-80% of the total mass of the components (A) to (C), and
   the blending amount of the polymerization initiator (C) is 0.1-10% of the total mass of the components (A) to (C).

2. The composition for hard tissue repair according to claim 1, wherein the polymer powder (B) comprises a polymer powder (B-x) having an aspect ratio of 1.10 or more and 1.90 or less, and the aspect ratio of all of the polymer powder (B) is 1.11 or more and 1.80 or less.

3. The composition for hard tissue repair according to claim 1, further comprising a contrast medium (X).

4. The composition for hard tissue repair according to claim 3, wherein the blending amount of the contrast medium (X) is 0.01-70% of the total mass of the components (A) to (C).

5. The composition for hard tissue repair according to claim 1, further comprising antimicrobial drug particles (Y).

6. The composition for hard tissue repair according to claim 5, wherein the blending amount of the antimicrobial drug particles (Y) is 0.01-30% of the total mass of the components (A) to (C).

7. A kit for hard tissue repair comprising three or more members, in which each of the components of the monomer (A), the polymer powder (B) and the polymerization initiator (C) contained in the composition for hard tissue repair according to claim 1 are divided and contained in the members separately or optionally in combination.

* * * * *